US006387652B1

(12) United States Patent
Haugland et al.

(10) Patent No.: US 6,387,652 B1
(45) Date of Patent: May 14, 2002

(54) METHOD OF IDENTIFYING AND QUANTIFYING SPECIFIC FUNGI AND BACTERIA

(75) Inventors: Richard Haugland, Middleton; Stephen Vesper, Kettering, both of OH (US)

(73) Assignee: U.S. Environmental Protection Agency, Washington, DC (US)

( * ) Notice: Subject to any disclaimer, the term of this patent is extended or adjusted under 35 U.S.C. 154(b) by 0 days.

(21) Appl. No.: 09/593,012

(22) Filed: Jun. 13, 2000

Related U.S. Application Data

(63) Continuation-in-part of application No. 09/290,990, filed on Apr. 14, 1999, now abandoned.
(60) Provisional application No. 60/081,773, filed on Apr. 15, 1998.

(51) Int. Cl.[7] .............................. C12Q 1/04; C12Q 1/00; C12Q 1/68; G01N 33/53
(52) U.S. Cl. .............................. 435/34; 435/4; 435/968; 435/973; 435/6; 435/254.1; 435/254.3; 435/254.5; 435/254.6; 435/848; 435/849; 435/913
(58) Field of Search .............................. 435/34, 4, 968, 435/973, 6, 254.1, 254.3, 254.5, 254.6, 254.8, 254.9, 256.1, 256.2, 256.3, 256.6, 256.7, 848, 849, 913

(56) References Cited

U.S. PATENT DOCUMENTS

| | | | | |
|---|---|---|---|---|
| 5,707,802 A | * | 1/1998 | Sandhu et al. | 435/6 |
| 5,876,930 A | | 3/1999 | Livak et al. | 435/6 |
| 5,919,617 A | * | 7/1999 | Bhattacharjee et al. | 435/6 |

OTHER PUBLICATIONS

Jansson et al, Molecular Biotechnology, V. 7, pp. 103–120, (1997).*
Batt, Carl A., "Molecular Diagnostics for Dairy–Borne Pathogens," Journal of Dairy Science, 1997, vol. 80, pp. 220–229.
Haugland et al., "Identification of Sequence–Specific PCR Primers for the Detection of the Toxigenic Fungal Species, *Stachybotrys chartarum*," Abstracts of the 97th General Meeting for the American Society for Microbiology, May 1997, vol. 97, pp. 507.

* cited by examiner

*Primary Examiner*—Louise N. Leary
(74) *Attorney, Agent, or Firm*—Browdy and Neimark

(57) ABSTRACT

Fungi and bacteria can be detected and rapidly quantified by using the nucleotide sequences taught here that are specific to the particular species or group of species of fungi or bacteria. Use of the sequences can be made with fluorescent labeled probes, such as in the TaqMan™ system which produces real time detection of polymerase chain reaction (PCR) products. Other methods of detection and quantification based on these sequences include hybridization, conventional PCR or other molecular techniques.

79 Claims, 4 Drawing Sheets

Example 1, Figure 1

Example 1, Figure 2

TaqMan Assay Validation.

The numbers of H. pylori cells present in an unknown sample can be determined from a standard curve of cycle threshold ($C^T$) values for DNA extracts from known quantities of these cells. TaqMan assay results expressed as $C^T$ values for DNA extracts of H. pylori cells over a range from 2 to $2 \times 10^7$ cells per assay are shown in Figure 4. Assay results were linear (R-squared = 0.990 over the range from $2 \times 10^2$ to $2 \times 10^7$ cells per assay and maintained a positive slope down to 2 cells per assay.

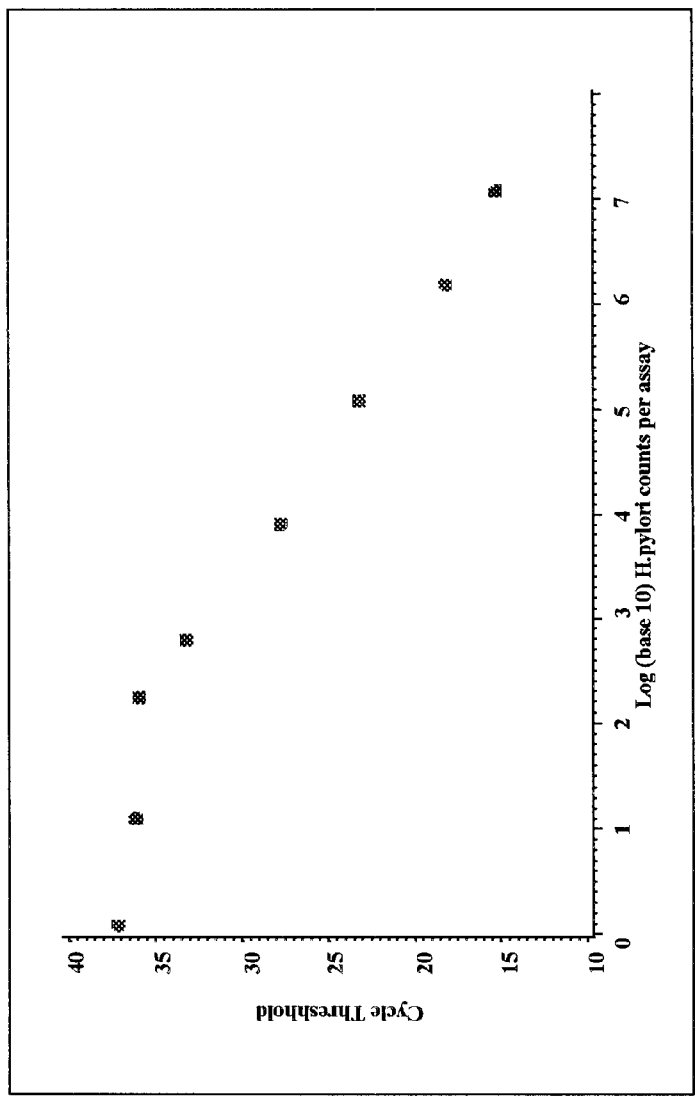

Figure 4. Log (base10) H. pylori cells per assay plotted against corresponding cycle threshold TaqMan values.

US 6,387,652 B1

METHOD OF IDENTIFYING AND QUANTIFYING SPECIFIC FUNGI AND BACTERIA

CROSS-REFERENCE TO RELATED APPLICATIONS

The present application is a continuation in part of Ser. No. 09/290,990, filed Apr. 14, 1999 now abanonded, which claims priority from provisional application Ser. No. 60/081,773, filed Apr. 15, 1998, the entire contents of both of which are hereby incorporated by reference.

FIELD OF THE INVENTION

The present invention relates to a method of identifying and quantifying specific fungi and bacteria using specific DNA sequences, as described and taught herein. These sequences can be used with real time detection of PCR products with a fluorogenic probe system or other molecular approaches like hybridizations.

BACKGROUND OF THE INVENTION

Fungi and bacteria are the source of or contribute to many health problems including infections, gastroenteritis, ulcers, asthma, allergies and sinusitis. The rapid identification of these microorganisms is critical for diagnosis and treatment. In addition, detecting and/or quantifying these microorganism in the environment may help to prevent adverse health effects.

Limitations of Current Technology

In order to determine the risk fungi and bacteria pose to human health, it is necessary to know what fungi and bacteria are present and in what numbers. Fungi and bacteria can be ingested, inhaled, or might enter the body through abrasions or punctures. It is important to identify these microorganisms as specifically and as rapidly as possible. Some species of a particular genus are harmless whereas others of the same genus may cause significant health effects. So without knowing precisely what microorganisms are present and in what numbers, it is impossible to evaluate the potential for negative health effects or the establishment of a risk assessment.

In the past, the detection and quantitative measurement of fungi and bacteria in samples has been performed either by direct microscopic examination of the collected cells or by growing cells on a suitable medium and identification and enumeration of the resultant colonies. The first method is highly labor intensive and is subject to potential errors in the recognition and positive identification. The second method is both time consuming and subject to significant quantitative inaccuracy. Both methods require extensive experience on the part of the analyst.

Some molecular approaches, such as the conventional polymerase chain reaction (PCR) procedure, are subject to inaccuracies due to the difficulty of quantifying the product. This procedure is also relatively slow and requires expertise in molecular biology.

SUMMARY OF THE INVENTION

It is an object of the present invention to overcome the aforesaid deficiencies in the prior art.

It is an object of the present invention to provide a simple, reliable method for detecting and quantifying some fungi and bacteria by using the nucleotide sequences specific to each species or group of species of fungi and bacteria, as described herein.

According to the present invention, fungi and bacteria can be identified and quantified by using a nucleotide sequence specific to the particular species or, in the case of some fungi, group of species. Many methods including using real time, probe-based detection of polymerase chain reaction (PCR) products (e.g. TaqMan™ system) or other methods of detection and quantification including hybridization or conventional PCR could be used with these sequences.

Theory

Each microorganism is unique because of the sequence of some of the nucleotides in its DNA. However, there are many sequences which are common to more than one organism. There is thus a hierarchy or classification into which all microorganisms can be arranged. The "species" are typically the finest level of distinction that is recognized for separation of different members of a given genus. In the past, species were separated on the basis of morphological or biochemical differences. In order to identify or separate different species on the basis of its DNA sequence, one finds sequences that are unique to a given species but at the same time common to all isolates of a given species.

For this invention the internal transcribed spacer (ITS) regions of nuclear ribosomal DNA (rDNA) of the different fungi were used. For the bacteria, the sequences of unique enzymes were chosen.

To apply this invention, a number of possible detection methods are possible. For example, the TaqMan™, 3'-5' exonuclease assay signals the formation of PCR amplicons by a process involving the nucleolytic degradation of a double-labeled fluorogenic probe that hybridizes to the target template at a site between the two primer recognition sequences (cf. U.S. Pat. No. 5,876,930). The model 7700 automates the detection and quantitative measurement of these signals, which are stoichiometrically related to the quantities of amplicons produced, during each cycle of amplification In addition to providing substantial reductions in the time and labor requirements for PCR analyses, this technology permits simplified and potentially highly accurate quantification of target sequences in the reactions.

There are additional systems and other molecular approaches that operate upon essentially the same principal. What is common to all of these technologies is the need for the identification of specific sequences that are unique to the targeted organism but common to all members of the species. The present invention teaches these identifying sequences and gives a description of the practical application of the sequences in the identification and quantification of specific fungi and bacteria.

BRIEF DESCRIPTION OF THE DRAWINGS

FIG. 4 shows *H. pylori* counts per assay plotted against cycle threshold values.

DETAILED DESCRIPTION OF THE INVENTION

DNA Extraction

Figure 1:
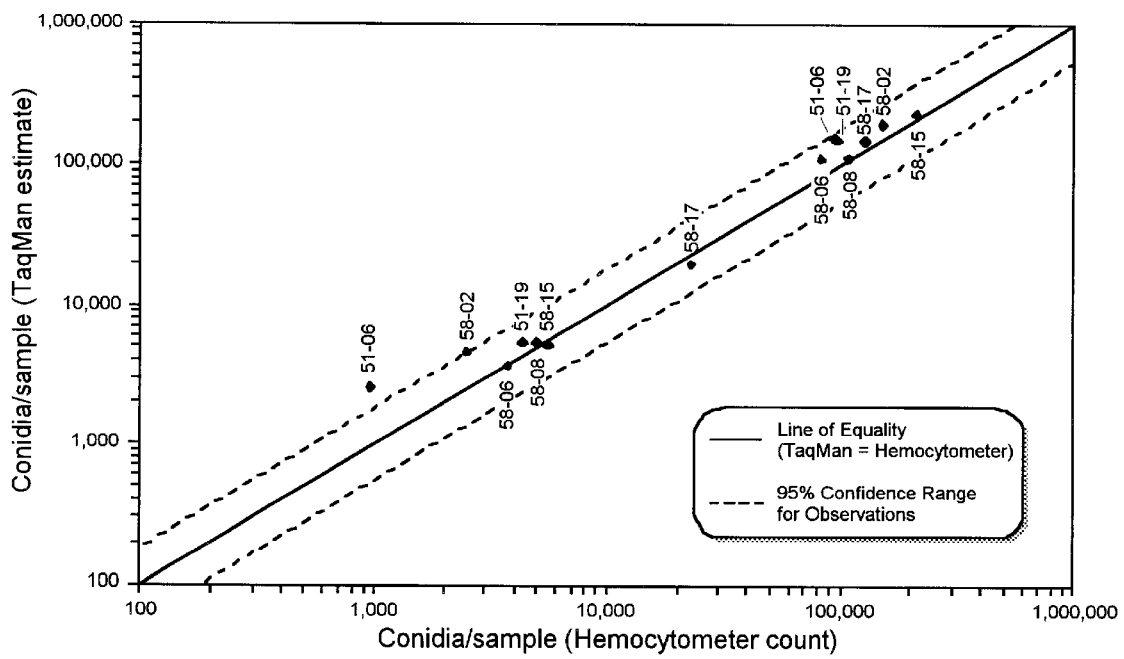
FIG. 1 illustrates the sensitivity of the assay of the present invention.

Genomic DNA is extracted using standard methods, e.g., the glass bead milling and glass milk adsorption method or any similar procedure of extracting genomic DNA.

Reactions are prepared in 0.5 ml thin-walled, optical grade PCR tubes (PE Applied Biosystems, Foster City Calif.) by addition of the following components; 12.5 µl of TaqMan Universal Master Mix (a 2×-concentrated, proprietary mixture of AmpliTaq Gold™ DNA polymerase, AmpErase® UNG, dNTPs with UTP, passive reference dye and optimized buffer components, PE Applied Biosystems, Foster City Calif.); 2.5 µl of a mixture of forward and reverse primers (10 nM each); 2.5 µl of 400 nM TaqMan probe; 2.5 µl of 2 mg/ml bovine serum albumin, fraction V (Sigma Chemical, St. Louis, Mo.) and 5 µl of DNA template.

For each targeted fungus or bacterium, the appropriate forward primer, reverse primer and probe (Tables 1 and 2) are to be obtained. The probe is labeled with an appropriate set of dyes or other markers for the particular system of measurement being used.

For each target species or group of species, a calibrator sample with a known number of conidia or cells is used as a standard. To ensure that the sample matrix does not affect the PCR reaction and, thus the quantitative results, an internal standard is used. Addition of these conidia or cells to both the test and calibrator samples normalize the target species or group for potential sample to sample variability in DNA extraction efficiencies.

TABLE 1

List of Fungal Primers and Probes

*Absidia coerulea/glauca*

Forward Primer NS92F: 5'-CACCGCCCGTCGCTAC (SEQ ID NO:1)

Reverse Primer AcoerR1: 5'-TCTAGTTTGCCATAGTTCTCTTCCAG (SEQ ID NO:2)

Probe MucP1: 5'-CCGATTGAATGGTTATAGTGAGCATATGGGATC (SEQ ID NO:3)

*Absidia corymbifera*

Forward Primer NS92F: 5'-CACCGCCCGTCGCTAC (SEQ ID NO:4)

Reverse Primer AcoryR1: 5'-GCAAAGCGTTCCGAAGGACA (SEQ ID NO:5)

Probe AcoryP1: 5'-ATGGCACGAGCAAGCATTAGGGACG (SEQ ID NO:6)

*Acremonium strictum*

Forward Primer AstrcF1: 5'-CAACCCATTGTGAACTTACCAAAC (SEQ ID NO:7)

Reverse Primer AstrcR1: 5'-CGCCCCTCAGAGAAATACGATT (SEQ ID NO:8)

Probe AstrcP1: 5'-TCAGCGCGCGGTGGCCTC (SEQ ID NO: 9)

*Alternaria alternata*

Forward Primer AaltrF1: 5'-GGCGGGCTGGAACCCTC (SEQ ID NO:10)

Reverse Primer AltrR1-1: 5'GCAATTACAAAAGGTTTATGTTTGTCGTA (SEQ ID NO:11)

Reverse Primer AaltrR1-2: 5'-TGCAATTACTAAAGGTTTATGTTTGTCGTA (SEQ ID NO:12)

Probe AaltrP1: 5'-TTACAGCCTTGCTGAATTATTCACCCTTGTCTTT (SEQ ID NO:13)

*Apophysomyces elegans* and *Saksenea vasiformis*

Forward Primer NS92F: 5'-CACCGCCCGTCGCTAC (SEQ ID NO:14)

Reverse Primer AelegR1: 5'-GACTCGAATGAGTTCTCGCTTC (SEQ ID NO:15)

Probe AelegP1: 5'-TGGCCAAGACCAGAATATGGGATTGC (SEQ ID NO:16)

*Aspergillus flavus/oryzae*

Forward Primer AflavF1: 5'-CGAGTGTAGGGTTCCTAGCGA (SEQ ID NO:17)

Reverse Primer AflavR1: 5'-CCGGCGGCCATGAAT (SEQ ID NO:18)

Probe AtlavP1: 5'-TCCCACCCGTGTTTACTGTACCTTAGTTGCT (SEQ ID NO:19)

*Aspergillus fumigatus, Neosartorya fischeri*

Forward Primer AfumiF1: 5'-GCCCGCCGTTTCGAC (SEQ ID NO:20)

Reverse Primer AfumiR1: 5'-CCGTTGTTGAAAGTTTTAACTGATTAC (SEQ ID NO:21)

Probe AfumiP1: 5'-CCCGCCGAAGACCCCAACATG (SEQ ID NO:22)

TABLE 1-continued

List of Fungal Primers and Probes

*Aspergillus niger/foetidus/phoenicus*

Forward Primer  AnigrF1: 5'-GCCGGAGACCCCAACAC-3' (SEQ ID NO:23)

Reverse Primer  AnigrR1: 5'-TGTTGAAAGTTTTAACTGATTGCATT-3' (SEQ ID NO:24)

Probe           AnigrP1: 5'-AATCAACTCAGACTGCACGCTTTCAGACAG (SEQ ID NO:25)

*Aspergillus nomius*

Forward Primer  AflavF1: 5'-CGAGTGTAGGGTTCCTAGCGA-3' (SEQ ID NO:26)

Reverse Primer  AnomiR1: 5'-CCGGCGGCCTTGC-3' (SEQ ID NO:27)

Probe           AflavP1: 5'-TCCCACCCGTGTTTACTGTACCTTAGTTGCT (SEQ ID NO:28)

*Aspergillus ochraceus/ostianus/auricomus*

Forward Primer  AochrF1: 5'-AACCTCCCACCCGTGTATACC-3' (SEQ ID NO:29)

Reverse Primer  AochrR1: 5'-CCGGCGAGCGCTGTG-3'(SEQ ID NO:30)

Probe           AochrP1: 5'-ACCTTGTTGCTTCGGCGAGCCC (SEQ ID NO:31)

*Aspergillus parasiticus/sojae*

Forward Primer  AflavF1: 5'-CGAGTGTAGGGTTCCTAGCGA-3' (SEQ ID NO:32)

Reverse Primer  AparaR3: 5'-GCCCGGGGCTGACG (SEQ ID NO:33)

Probe           AflavP1: 5'-TCCCACCCGTGTTTACTGTACCTTAGTTGCT (SEQ ID NO:34)

*Aspergillus restrictus/caesillus/conicus*

Forward Primer  ArestF2: 5'-CGGGCCCGCCTTCAT-3' (SEQ ID NO:35)

Reverse Primer  ArestR1: 5'-GTTGTTGAAAGTTTTAACGATTTTTCT (SEQ ID NO:36)

Probe           ArestP1: 5'-CCCGCCGGAGACTCCAACATTG (SEQ ID NO:37)

*Aspergillus sydowii*

Forward Primer  AsydoE1: 5'-CAACCTCCCACCCGTGAA (SEQ ID NO:38)

Reverse Primer  versR1: 5'-CCATTGTTGAAAGTTTTGACTGATTTTA (SEQ ID NO:39)

Probe           versP1: 5'-AGACTGCATCACTCTCAGGCATGAAGTTCAG (SEQ ID NO:40)

*Aspergillus tamarii*

Forward Primer  AflavF1: 5'-CGAGTGTAGGGTTCCTAGCGA (SEQ ID NO: 41)

Reverse Primer  AtamaR1: 5'-CCCGGCGGCCTTAA (SEQ ID NO:42)

Probe           AflavP1: 5'-TCCCACCCGTGTTTACTGTACCTTAGTTGCT (SEQ ID NO:43)

*Aspergillus terreus*

Forward Primer  AterrF1: 5'-TTACCGAGTGCGGGTCTTTA (SEQ ID NO:44)

Reverse Primer  AterrR1: 5'-CGGCGGCCAGCAAC (SEQ ID NO:45)

Probe           AterrP1: 5'-AACCTCCCACCCGTGACTATTGTACCTTG (SEQ ID NO:46)

*Aspergillus ustus*

Forward Primer  AustsF1: 5'-GATCATTACCGAGTGCAGGTCT (SEQ ID NO:47)

Reverse Primer  AustsR1: 5'-GCCGAAGCAACGTTGGTC (SEQ ID NO:48)

Probe           AustsP1: 5'-CCCCCGGGCAGGCCTAACC (SEQ ID NO:49)

*Aspergillus versicolor*

Forward Primer  AversF2: 5'-CGGCGGGGAGCCCT (SEQ ID NO:50)

Reverse Primer  versR1: 5'-CCATTGTTGAAAGTTTTGACTGATTTTA (SEQ ID NO:51)

TABLE 1-continued

List of Fungal Primers and Probes

Probe      versP1: 5'-AGACTGCATCACTCTCAGGCATGAAGTTCAG (SEQ ID NO:52)

*Chaetomium globosum*

Forward Primer    CglobF1: 5'-CCGCAGGCCCTGAAAAG (SEQ ID NO:53)

Reverse Primer    CglobR1: 5'-CGCGGCGCGACCA (SEQ ID NO:54)

Probe      CglobP1: 5'-AGATGTATGCTACTACGCTCGGTGCGACAG (SEQ ID NO:55)

*Cladosporium cladosporioides*

Type 1

Forward Primer    Cclad1F1: 5'-CATTACAAGTGACCCCGGTCTAAC (SEQ ID NO:56)

Reverse Primer    CcladR1: 5'-CGCGGCGCGACCA (SEQ ID NO:57)

Probe      CcladP1: 5'-CCGGGATGTTCATAACCCTTTGTTGTCC (SEQ ID NO:58)

Type 2
Forward Primer    Cclad2F1: 5'-TACAAGTGACCCCGGCTACG (SEQ ID NO:59)

Reverse Primer    CcladR1: 5'-CCCCGGAGGCAACAGAG (SEQ ID NO:60)

Probe      CcladP1: 5'-CCGGGATGTTCATAACCCTTTGTTGTCC (SEQ ID NO:61)

*Cladosporium herbarum*

Forward Primer    CherbF1: 5'-AAGAACGCCCGGGCTT (SEQ ID NO:62)

Reverse Primer    CherbR1: 5'-CGCAAGAGTTTGAAGTGTCCAC (SEQ ID NO:63)

Probe      CherbP1: 5'-CTGGTTATTCATAACCCTTTGTTGTCCGACTCTG (SEQ ID NO:64)

*Cladosporium sphaerospermum*

Forward Primer    CsphaF1: 5'-ACCGGCTGGGTCTTTCG (SEQ ID NO:65)

Reverse Primer    CsphaR1: 5'-GGGGTTGTTTTACGGCGTG (SEQ ID NO:66)

Probe      CsphaP1: 5'-CCCGCGGCACCCTTTAGCGA (SEQ ID NO:67)

*Conidiobolus coronatus/incongruus*

Forward Primer    NS92F: 5'-CACCGCCCGTCGCTAC (SEQ ID NO:68)

Reverse Primer    ConiR1: 5'-TGACCAAGTTTGACCAATTTCTCTA (SEQ ID NO:69)

Probe      ConiP1: 5'-ATGGTTTAGTGAGGCCTCTGGATTTGAAGCTT (SEQ ID NO:70)

*Cunninghamella elegans*

Forward Primer    NS92F: 5'-CACCGCCCGTCGCTAC (SEQ ID NO:71)

Reverse Primer    CunR1: 5'-AATCTAGTTTGCCATAGTTCTCCTCA (SEQ ID NO:72)

Probe      CunP1: 5'-TGAATGGTCATAGTGAGCATGTGGGATCTTT (SEQ ID NO:73)

*Emericella nidulans/rugulosa/quadrilineata*

Forward Primer    AversF1: 5'-CAACCTCCCACCCGTGAC (SEQ ID NO:74)

Reverse Primer    AniduR1: 5'-CATTGTTGAAAGTTTTGACTGATTTGT (SEQ ID NO:75)

Probe      versP1: 5'-AGACTGCATCACTCTCAGGCATGAAGTTCAG (SEQ ID NO:76)

*Eurotium amstelodami/chevalieri/herbariorum/rubrum/repens*

Forward Primer    EamstF1: 5'-GTGGCGGCACCCATGTCT (SEQ ID NO:77)

Reverse Primer    EamstR1: 5'-CTGGTTAAAAAGATTGGTTGCGA (SEQ ID NO:78)

Probe      EamstP1: 5'-CAGCTGGACCTACGGGAGCGGG (SEQ ID NO:79)

TABLE 1-continued

List of Fungal Primers and Probes

*Epicoccum nigrum*

| Forward Primer | EnigrF1: 5'-TTGTAGACTTCGGTCTGCTACCTCTT (SEQ ID NO:80) |
| Reverse Primer | EnigrR1: 5'-TGCAACTGCAAAGGGTTTGAAT (SEQ ID NO:81) |
| Probe | EnigrP1: 5'-CATGTCTTTTGAGTACCTTCGTTTCCTCGGC (SEQ ID NO:82) |

*Geotrichum candidum* strain UAMH 7863

Forward Primer   GeoF1: 5'-GATATTTCTTGTGAATTGCAGAAGTGA (SEQ ID NO:83)

Reverse Primer   GeoR1: 5'-TTGATTCGAAATTTTAGAAGAGCAAA (SEQ ID NO:84)

Probe            GeoP1: 5'-CAATTCCAAGAGAGAAACAACGCTCAAACAAG (SEQ ID NO:85)

Geotrichum candidum

Forward Primer   NS92F: 5'-CACCGCCCGTCGCTAC (SEQ ID NO:86)

Reverse Primer   GcandR1: 5'-AGAAAAGTTGCCCTCTCCAGTT (SEQ ID NO:87)

Probe            GeoP2: 5'-TCAATCCGGAAGCCTCACTAAGCCATT (SEQ ID NO:88)

*Geotrichum klebahnii*

Forward Primer   NS92F: 5'-CACCGCCCGTCGCTAC (SEQ ID NO:89)

Reverse Primer   GklebR1: 5'-AAAAGTCGCCCTCTCCTGC (SEQ ID NO:90)

Probe            GeoP2: 5'-TCAATCCGGAAGCCTCACTAAGCCATT (SEQ ID NO:91)

*Memnoniella echinata*

Forward Primer   StacF4 5'-TCCCAAACCCTTATGTGAACC (SEQ ID NO:92)

Reverse Primer   MemR1: 5'-TGTTTATACCACTCAGACGATACTCAAGT (SEQ ID NO:93)

Probe            MemP1: 5'-CTCGGGCCCGGAGTCAGGC (SEQ ID NO:94)

*Mortierella polycephala/wolfii*

Forward Primer   NS92F: 5'-CACCGCCCGTCGCTAC (SEQ ID NO:95)

Reverse Primer   MortR1: 5'-TGACCAAGTTTGGATAACTTTTCAG (SEQ ID NO:96)

Probe            MortP1: 5'-CTTAGTGAGGCTTTCGGATTGGATCTAGGCA (SEQ ID NO:97)

*Mucor mucedo*

Forward primer   NS92F: 5'-CACCGCCCGTCGCTAC (SEQ ID NO:98)

Reverse Primer   MmuceR1: 5'-CTAAATAATCTAGTTTGCCATAGTTTTCG (SEQ ID NO:99)

Probe            MucP1: 5'-CCGATTGAATGGTTATAGTGAGCATATGGGATC (SEQ ID NO:100)

*Mucor amphibiorum/circinelloides/heimalis/indicus/mucedo/racemosus/ramosissimus* and *Rhizopus azygosporus/homothalicus/microsporus/oligosporus/oryzae*

Forward Primer   NS92F: 5'-CACCGCCCGTCGCTAC (SEQ ID NO:101)

Reverse Primer   MucR1-1: 5'-CCTAGTTTGCCATAGTTCTCAGCAG (SEQ ID NO:102)

Probe            MucP1: 5'-CCGATTGAATGGTTATAGTGAGCATATGGGATC (SEQ ID NO:103)

*Myrothecium verrucaria/roridum*

Forward Primer   MyroF1: 5'-AGTTTACAAACTCCCAAACCCTTT (SEQ ID NO:104)

Reverse Primer   MyroR1: 5'-GTGTCACTCAGAGGAGAAAACCA (SEQ ID NO:105)

Probe            MyroP1: 5'-CGCCTGGTTCCGGGCCC (SEQ ID NO:106)

TABLE 1-continued

List of Fungal Primers and Probes

*Paecilomyces lilacinus*

Forward Primer    PlilaF1: 5'-CCCACTGTGAACCTTACCTCAG (SEQ ID NO:107)

Reverse Primer    PlilaR1: 5'-GCTTGTGCAACTCAGAGAAGAAAT (SEQ ID NO:108)

Probe             PlilaP1: 5'-CCGCCCGCTGGGCGTAATG (SEQ ID NO:109)

*Paecilomyces variotii*

Forward Primer    PvariF1: 5'-CCCGCCGTGGTTCAC (SEQ ID NO:110)

Forward Primer    PvariF2: 5'-CGAAGACCCCTGGAACG (SEQ ID NO:111)

Reverse Primer    PvariR1: 5'-GTTGTTGAAAGTTTTAATTGATTGATTGT (SEQ ID NO:112)

Probe             PvariP1: 5'-CTCAGACGGCAACCTTCCAGGCA (SEQ ID NO:113)

*Penicillium aurantiogriseum/polonicum/viridicatum/freii/verrucosum\*/hirsutum*

Forward Primer    PauraF1: 5'-CGGGCCCGCCTTTAC (SEQ ID NO:114)

Reverse Primer    PauraR1-1: 5'-GAAAGTTTTAAATAATTTATATTTTCACTCAGAGTT (SEQ ID NO:115)

Probe             PenP2: 5'-CGCGCCCGCCGAAGACA (SEQ ID NO:116)

*Penicillium aurantiogriseum/polonicum/viridicatum/freii*

Forward Primer    PauraF2: 5'-ACCGAGTGAGGGCCCTT (SEQ ID NO:117)

Reverse Primer    PauraR6: 5'-CCCGGCGGCCAGTA (SEQ ID NO:118)

Probe             PenP3: 5'-TCCAACCTCCCACCCGTGTTTATTT (SEQ ID NO:119)

*Penicillium brevicompactum\*/alberechii*

Forward Primer    PbrevF1: 5'-CCTTGTTGCTTCGGCGA (SEQ ID NO:120)

Reverse Primer    PbrevR2: 5'-TCAGACTACAATCTTCAGACAGAGTTCTAA (SEQ ID NO:121)

Probe             PbrevP1: 5'-CCTGCCTTTTGGCTGCCGGG (SEQ ID NO:122)

*Penicillium chrysogenum/griseofulvum/glandicola/coprophilum/expansum and Eupenicillium crustaceum/egyptiacum*

Forward Primer    PchryF1: 5'-CGGGCCCGCCTTAAC (SEQ ID NO:123)

Reverse Primer    PchryR1-1: 5'-GAAAGTTTTAAATAATTTATATTTTCACTCAGAGTA (SEQ ID NO:124)

Reverse Primer    PchryR2-1: 5'-GAAAGTTTTAAATAATTTATATTTTCACTCAGACCA (SEQ ID NO:125)

Probe             PenP2: 5'-CGCGCCCGCCGAAGACA (SEQ ID NO:126)

*Penicillium citrinum/sartoryi/westlingi*

Forward Primer    PcitrF1: 5'-CCGTGTTGCCCGAACCTA (SEQ ID NO:127)

Reverse Primer    PcitrR1: 5'-TTGTTGAAAGTTTTAACTAATTTCGTTATAG (SEQ ID NO:128)

Probe             PcitrP2: 5'-CCCCTGAACGCTGTCTGAAGTTGCA (SEQ ID NO:129)

*Penicillium corylophilum*

Forward Primer    PcoryF1: 5'-GTCCAACCTCCCACCCA (SEQ ID NO:130)

Reverse Primer    PcoryR3-1: 5'-GCTCAGACTGCAATCTTCAGACTGT (SEQ ID NO:131)

Probe             PcoryP1: 5'-CTGCCCTCTGGCCCGCG (SEQ ID NO:132)

*Penicillium decumbens*

Forward Primer    PdecuF3: 5'-GGCCTCCGTCCTCCTTTG (SEQ ID NO:133)

Reverse Primer    PdecuR3: 5'-AAAAGATTGATGTGTTCGGCAG (SEQ ID NO:134)

TABLE 1-continued

List of Fungal Primers and Probes

| | |
|---|---|
| Probe | PdecuP2: 5'-CGCCGGCCGGACCTACAGAG (SEQ ID NO:135) |

*Penicillium echinulatum/solitum/camembertii/commune/crustosum*

| | |
|---|---|
| Forward Primer | PchryF1: 5'-CGGGCCCGCCTTAAC (SEQ ID NO:136) |
| Reverse Primer | PauraR1-1: 5'-GAAAGTTTTAAATAATTTATATTTTCACTCAGAGTT (SEQ ID NO:137) |
| Probe | PenP2: 5'-CGCGCCCGCCGAAGACA (SEQ ID NO:138) |

*Penicillium expansum/coprophilum*

| | |
|---|---|
| Forward Primer | PauraF2: 5'-ACCGAGTGAGGGCCCTT (SEQ ID NO:139) |
| Reverse Primer | PchryR6: 5'-CCCGGCGGCCAGTT (SEQ ID NO:140) |
| Probe | PenP3: 5'-TCCAACCTCCCACCCGTGTTTATTT (SEQ ID NO:141) |

*Penicillium fellutanum/charlesii*

| | |
|---|---|
| Forward Primer | PfellF1: 5'-AACCTCCCACCCGTGTATACTTA (SEQ ID NO:142) |
| Reverse Primer | PfellR1: 5'-CTTATCGCTCAGACTGCAAGGTA (SEQ ID NO:143) |
| Probe | PfellP1: CGGTTGCCCCCCGGCG (SEQ ID NO:144) |

*Penicillium janthinellum/raperi*

| | |
|---|---|
| Forward Primer | PjantF2: 5'-CCCACCCGTGTTTATCATACCTA (SEQ ID NO:145) |
| Reverse Primer | PjantR2: 5'-TTGAAAGTTTTAACTGATTTAGCTAATCG (SEQ ID NO:146) |
| Probe | PjantP2: 5'-TGCAATCTTCAGACAGCGTTCAGGG (SEQ ID NO:147) |

*Penicillium madriti/gladioli*

| | |
|---|---|
| Forward Primer | PauraF1: 5'-CGGGCCCGCCTTTAC (SEQ ID NO:148) |
| Reverse Primer | PchryR1-1: 5'-GAAAGTTTTAAATAATTTATATTTTCACTCAGAGTA (SEQ ID NO:149) |
| Reverse Primer | PchryR2-1: 5'-GAAAGTTTTAAATAATTTATATTTTCACTCAGACCA (SEQ ID NO:150) |
| Probe | PenP2: 5'-CGCGCCCGCCGAAGACA (SEQ ID NO:151) |

*Penicillium Oxalicum*

| | |
|---|---|
| Forward Primer | PoxalF1: 5'-GGGCCCGCCTCACG (SEQ ID NO:152) |
| Reverse Primer | PoxalR1: 5'-GTTGTTGAAAGTTTTAACTGATTTAGTCAAGTA (SEQ ID NO:153) |
| Probe | PoxalP1: 5'-ACAAGAGTTCGTTTGTGTGTCTTCGGCG (SEQ ID NO:154) |

*Penicillium roquefortii*

| | |
|---|---|
| Forward Primer | PchryF1: 5'-CGGGCCCGCCTTAAC (SEQ ID NO:155) |
| Reverse Primer | ProquR2: 5'-TTAAATAATTTATATTTGTTCTCAGACTGCAT (SEQ ID NO:156) |
| Probe | PenP2: 5'-CGCGCCCGCCGAAGACA (SEQ ID NO:157) |

*Penicillium simplicissimum/ochrochloron*

| | |
|---|---|
| Forward Primer | PsimpF1-1: 5'-AACCTCCCACCCGTGTTGATT (SEQ ID NO:158) |
| Reverse Primer | PsimpR2-1: 5'-GAGATCCGTTGTTGAAAGTTTTATCTG (SEQ ID NO:159) |
| Reverse Primer | PsimpR3-1: 5'-GAGATCCGTTGTTGAAAGTTTTAACAG (SEQ ID NO:160) |
| Probe | PsimpP1: 5'-CCGCCTCACGGCCGCC (SEQ ID NO:161) |

*Penicillium spinulosum/glabrum/thomii/pupurescens*
and *Eupenicillium lapidosum*

| | |
|---|---|
| Forward Primer | PspinF1: 5'-GTACCTTGTTGCTTCGGTGC (SEQ ID NO:162) |
| Reverse Primer | PspinR1: 5'-CGTTGTTGAAAGTTTTAACTTATTTAGTTTAT (SEQ ID NO:163) |

TABLE 1-continued

List of Fungal Primers and Probes

Probe              PspinP1: 5'-TCCGCGCGCACCGGAG (SEQ ID NO:164)

*Rhizomucor miehei/pusillus/variabilis*

Forward Primer   NS92F: 5'-CACCGCCCGTCGCTAC (SEQ ID NO:165)

Reverse Primer   RmucR1: 5'-GTAGTTTGCCATAGTTCGGCTA (SEQ ID NO:166)

Probe              RmucP1: 5'-TTGAATGGCTATAGTGAGCATATGGGAGGCT (SEQ ID NO:167)

*Rhizopus stolonifer*

Forward Primer NS92F: 5'-CACCGCCCGTCGCTAC (SEQ ID NO:168)

Reverse Primer RstolR1: 5'-GCTTAGTTTGCCATAGTTCTCTAACAA (SEQ ID NO:169)

Probe MucP1: 5'-CCGATTGAATGGTTATAGTGAGCATATGGGATC (SEQ ID NO:170)

*Scopulariopsis asperula*

Forward Primer   SCbrvF1: 5'-CCCCTGCGTAGTAGATCCTACAT (SEQ ID NO:171)

Reverse Primer   SCasprR1: 5'-TCCGAGGTCAAACCATGAGTAA (SEQ ID NO:172)

Probe              ScopP1: 5'-TCGCATCGGGTCCCGGCG (SEQ ID NO:173)

*Scopulariopsis brevicaulis/fusca*

Forward Primer   SCbrvF1: 5'-CCCCTGCGTAGTAGATCCTACAT (SEQ ID NO:174)

Reverse Primer   SCbrvR1: 5'-TCCGAGGTCAAACCATGAAATA (SEQ ID NO:175)

Probe              ScopP1: 5'-TCGCATCGGGTCCCGGCG (SEQ ID NO:176)

*Scopulariopsis brumptii*

Forward Primer   SCbrmF1: 5'-CCCCTGCGTAGTAGTAAAACCA (SEQ ID NO:177)

Reverse Primer   SCbrmR1: 5'-CCGAGGTCAAACATCTTTGG (SEQ ID NO:178)

Probe              ScopP1: 5'-TCGCATCGGGTCCCGGCG (SEQ ID NO:179)

*Scopulariopsis chartarum*

Forward Primer   SCchrF1: 5'-CCCCCTGCGTAGTAGTAAAGC (SEQ ID NO: 180)

Reverse Primer   SCchrR1: 5'-TCCGAGGTCAAACCATCAAG (SEQ ID NO:181)

Probe              ScopP1: 5'-TCGCATCGGGTCCCGGCG (SEQ ID NO:182)

*Scopulariopsis sphaerospora*

Forward Primer   SCsphF1: 5'-CCCCCTGCGTAGTAGTTTACAA (SEQ ID NO:183)

Reverse Primer   SCsphR1: 5'-CCGAGGTCAAACCATCAAAAG (SEQ ID NO:184)

Probe              ScopP1: 5'-TCGCATCGGGTCCCGGCG (SEQ ID NO:185)

*Stachybotrys chartarum*

Forward Primer   StacF4 TCCCAAACCCTTATGTGAACC (SEQ ID NO:186)

Reverse Primer   StacR5 GTTTGCCACTCAGAGAATACTGAAA (SEQ ID NO:187)

Probe              StacP2 CTGCGCCCGGATCCAGGC (SEQ ID NO:188)

*Trichoderma asperellum/hamatum*

Forward Primer   TasprF1: 5'-CCCAAACCCAATGTGAACGT (SEQ ID NO:189)

Reverse Primer   TasprR2-1: 5'-GGACTACAGAAAGAGTTTGGTTGCTT (SEQ ID NO:190)

Probe              TridP1: 5'-CCAAACTGTTGCCTCGGCGGG (SEQ ID NO:191)

*Trichoderma asperellum/hamatuim/viride**

TABLE 1-continued

List of Fungal Primers and Probes

| | | |
|---|---|---|
| Forward Primer | TasprF1: | 5'-CCCAAACCCAATGTGAACGT (SEQ ID NO:192) |
| Reverse Primer | TasprR1: | 5'-TTTGCTCAGAGCTGTAAGAAATACG (SEQ ID NO:193) |
| Probe | TridP1: | 5'-CCAAACTGTTGCCTCGGCGGG (SEQ ID NO:194) |

*Trichoderma harzianum*

| | | |
|---|---|---|
| Forward Primer | TharzF1: | 5'-TTGCCTCGGCGGGAT (SEQ ID NO:195) |
| Reverse Primer | TharzR1: | 5'-ATTTTCGAAACGCCTACGAGA (SEQ ID NO:196) |
| Probe | TharzP1: | 5'-CTGCCCCGGGTGCGTCG (SEQ ID NO:197) |

*Trichoderma longibrachiatum/citroviride*

| | | |
|---|---|---|
| Forward Primer | TlongF1: | 5'-TGCCTCGGCGGGATTC (SEQ ID NO:198) |
| Reverse Primer | TlongR1: | 5'-CGAGAAAGGCTCAGAGCAAAAT (SEQ ID NO:199) |
| Probe | TlongP1: | 5'-TCGCAGCCCCGGATCCCA (SEQ ID NO:200) |

*Trichoderma viride\*/atroviride/koningii*

| | | |
|---|---|---|
| Forward Primer | TviriF1: | 5'-CCCAAACCCAATGTGAACCA (SEQ ID NO:201) |
| Reverse Primer | TviriR1: | 5'-TCCGCGAGGGGACTACAG (SEQ ID NO:202) |
| Probe | TridP1: | 5'-CCAAACTGTTGCCTCGGCGGG (SEQ ID NO:203) |

*Ulocladium atrum/chartarum*

| | | |
|---|---|---|
| Forward Primer | UatrmF1: | 5'-GCGGGCTGGCATCCTT (SEQ ID NO:204) |
| Reverse Primer | UatrmR1: | 5'-TTGTCCTATGGTGGGCGAA (SEQ ID NO:205) |
| Probe | UloP1: | 5'-TGAATTATTCACCCGTGTCTTTTGCGTACTTCT (SEQ ID NO:206) |

*Ulocladium botrytis*

| | | |
|---|---|---|
| Forward Primer | UbotrF1: | 5'-CCCCCAGCAGTGCGTT (SEQ ID NO:207) |
| Reverse Primer | UbotrR1: | 5'-CTGATTGCAATTACAAAAGGTTTATG (SEQ ID NO:208) |
| Probe | UloP1: | 5'-TGAATTATTCACCCGTGTCTTTTGCGTACTTCT (SEQ ID NO:209) |

*Wallemia sebi*

| | | |
|---|---|---|
| WsebiF1: | | 5'-GGCTTAGTGAATCCTTCGGAG (SEQ ID NO:210) |
| WsebiR1: | | 5'-GTTTACCCAACTTTGCAGTCCA (SEQ ID NO:211) |
| WsebiP1: | | 5'-TGTGCCGTTGCCGGCTCAAATAG (SEQ ID NO:212) |

Universal Fungal

ASSAY 1

| | | |
|---|---|---|
| Forward Primer | 5.8F1: | 5'-AACTTTCAACAACGGATCTCTTGG (SEQ ID NO:213) |
| Reverse Primer | 5.8R1: | 5'-GCGTTCAAAGACTCGATGATTCAC (SEQ ID NO:214) |
| Probe | 5.8P1: | 5'-CATCGATGAAGAACGCAGCGAAATGC (SEQ ID NO:215) |

ASSAY 2

| | | |
|---|---|---|
| Forward Prime | NS92F: | 5'-CACCGCCCGTCGCTAC (SEQ ID NO:216) |
| Reverse Primer | ZygR1: | 5'-TAATGATCCTTCCGCAGGTTC (SEQ ID NO:217) |
| Probe | ZygP1: | 5'-CCTACGGAAACCTTGTTACGACTTTTACTTCCTCTAAA (SEQ ID NO:218) |

*Assay does not detect all strains of the indicated species

TABLE 2

List of Bacterial Primers and Probes

*Escherichia coli*

| | | |
|---|---|---|
| Forward Primer | uidAF1: | 5'-GGGCAGGCCAGCGTATC (SEQ ID NO:219) |
| Reverse Primer | uidAR1: | 5'-CCCACACTTTGCCGTAATGA (SEQ ID NO:220) |
| Reverse Primer | uidAR2: | 5'-CGTACACTTTTCCCGGCAAT (SEQ ID NO:221) |
| Probe | uidAP1: | 5'-TGCTGCGTTTCGATGCGGTCA (SEQ ID NO:222) |

*Helicobacter pylorii*

| | | |
|---|---|---|
| Forward Primer | HpylF1: | 5'-GGGTATTGAAGCGATGTTTCCT (SEQ ID NO:223) |
| Reverse Primer | HpylR1: | 5'-GCTTTTTTGCCTTCGTTGATAGT (SEQ ID NO:224) |
| Probe | HpylP1: | 5'-CTCGTAACCGTGCATACCCCTATTGAG (SEQ ID NO:225) |

One skilled in the art will appreciate that primers and/or probes can be used which are not identical to the ones described above, as long as there is substantial similarity between the sequences. For purposes of the present invention, "substantial similarity" means that more than 90–110% of the sequence is the same as the sequences enumerated above.

Performance of Assay

Standard procedures for the operation of the model 7700 or similar detection system are used. This includes, for example with the model 7700, use of all default program settings with the exception of reaction volume which was changed from 50 to 25 µl. Thermal cycling conditions consisting of two min at 50° C. 10 min at 95° C., followed by 40 cycles of 15 sec at 95° C. and 1 min at 60° C. Cycle threshold ($C_T$) determinations, i.e. non-integer calculations of the number of cycles required for reporter dye fluorescence resulting from the synthesis of PCR products to become significantly higher than background fluorescence levels were automatically performed by the instrument for each reaction using default parameters. Assays for fungal target sequences and *G. candidum* (reference) sequences in the same DNA samples are performed in separate reaction tubes.

Quantification of Fungal or Bacterial Target

Quantification is performed by first subtracting mean reference sequence $C_T$ values from mean target sequence $C_T$ values for both test samples and a pre-specified calibrator sample to obtain $\Delta C_T$ values. Calibrator sample $\Delta C_T$ values are then subtracted from $\Delta C_T$ values of the test samples to obtain $\Delta\Delta C_T$ values. Assuming an amplification efficiency of one (i.e. a doubling of the target sequence for each cycle), the ratio of target sequences in the test and calibrator samples is given by $2^{-\Delta\Delta C_T}$. (If the efficiency is less than one, then the new amplification efficiency value is used instead of 2.) For example, a ratio of 0.1, calculated in this manner, would indicate that the target sequence level in the test sample is one-tenth the level found in the calibrator sample. A direct comparison ($\Delta C_T$) approach should allow the discrimination of 1-fold differences in the quantities of target sequences in different samples with 95% confidence.

SPECIFIC EXAMPLES

Example 1

Quantitative Measurement of *Stachybotrys chartarum* conidia using Real Time Detection of PCR Products with the TaqMan™ Fluorogenic Probe System Conidial stocks of the target fungus, e. g. *Stachybotrys chartarum*, and the reference target, e.g. *Geotrichum candidum*, were prepared to act as calibrator and internal standard, respectively.

Genomic DNAs were extracted from 20 µl conidial suspensions using a glass bead milling and glass milk adsorption method. Briefly, this method involved mixing test and reference conidia suspensions (10 µl ea.) with 0.3 g of acid-washed glass beads (G-1277; Sigma, St. Louis, Mo.) and 10 µl, 100 µl and 300 µl, respectively, of glass milk suspension, lysis buffer and binding buffer from an Elu-Quik DNA purification kit (Schleicher and Schuell, Keene, N.H.) in sterile 2 ml conical bottom, screw cap tubes (506–636; PGC Scientifics, Gaithersburg, Md.). The tubes were shaken in a mini beadbeater (Biospec Products, Bartlesville, Okla.) for one minute at maximum rate and DNAs were recovered in final volumes of 200 µl distilled water after performing a slight modification of the small-scale protocol provided with the Elu-Quik purification kit.

The TaqMan probes and primers were obtained from the custom oligonucleotide synthesis facility at PE-Applied Biosystems (Foster City, Calif.). TaqMan probes contained a TAMRA group conjugated to their 3'-terminal nucleotide and a FAM group linked to their 5'-terminal nucleotides as the quencher and reporter fluorochromes, respectively. For *Geotrichum candidum*, the forward primer is NS92F: 5'-CACCGCCCGTCGCTAC (SEQ ID NO:86), the reverse primer is GcandR1: 5'-AGAAAAGTTGCCCTCTCCAGTT (SEQ ID NO:87), and the probe is GeoP2: 5'-TCAATCCGGAAGCCTCACTAAGCCATT (SEQ ID NO:88). For *Stachybotrys chartarum*, the forward primer is StacF4 5'-TCCCAAACCCTTATGTAACC (SEQ ID NO:186), the reverse primer is StacR5 5'-GTTTGCCACTCAGAGAATACTGAAA (SEQ ID NO:187), and the probe is StacP2 5'-CTGCGCCCGGATCCAGGC (SEQ ID NO:188).

PCR reactions were prepared in 0.5 ml thin-walled, optical grade PCR tubes (PE Applied Biosystems, Foster City Calif.) by addition of the following components: 12.5 µl of TaqMan Universal Master Mix, a 2×concentrated, proprietary mixture of AmpliTaq Gold™ DNA polymerase, AmpErase® UNG, dNTPs with UTP, passive reference dye and optimized buffer components (PE Applied Biosystems, Foster City Calif.); 2.5 µl of a mixture of forward and reverse primers (10 nM each); 2.5 µl of 400 nM TaqMan probe; 2.5 µl of 2 mg/ml bovine serum albumin (fraction V, Sigma Chemical, St. Louis, Mo.) and 5 µl of DNA template.

Standard procedures for the operation of the model 7700, as described in the instrument's manual, were followed. This included the use of all default program settings with the exception of reaction volume which was changed from 50 to 25 μl. Thermal cycling conditions consisting of two min at 50° C., 10 min at 95° C., followed by 40 cycles of 15 sec at 95° C. and 1 min at 60° C. Cycle threshold ($C_T$) determinations, i.e. non-integer calculations of the number of cycles required for reporter dye fluorescence resulting from the synthesis of PCR products to become significantly higher than background fluorescence levels were automatically performed by the instrument for each reaction using default parameters. Assays for *S. chartarum* (target) sequences and *G. candidum* (reference) sequences in the same DNA samples were performed in separate reaction tubes.

Quantitation of *S. chartarum* conidia using the comparative $C_T$ method. was performed by first subtracting mean reference sequence $C_T$ values from mean target sequence $C_T$ values for both test samples and a pre-specified calibrator sample to obtain $\Delta C_T$ values. Calibrator sample $\Delta C_T$ values are then subtracted from $\Delta C_T$ values of the test samples to obtain $\Delta\Delta C_T$ values.

Calibrator samples were DNA extracts from mixtures of approximately $2\times10^4$ *S. chartarum* (strain UMAH 6417) and $2\times10^5$ *G. candidum* conidia. Test samples were mixed with the same quantity of *G. candidum* conidia prior to DNA extraction. Ratios of target sequences determined in the test and calibrator samples were then multiplied by the known quantities of *S. chartarum* conidia in the calibrator samples to obtain estimates of the absolute quantities of these conidia in the test samples.

Each series of DNA extracts was also analyzed using only *S. chartarum* target sequence assay results. In these calculations, calibrator sample $C_T$ values were subtracted directly from corresponding test sample $C_T$ values to obtain $\Delta C_{T,STAC}$ values. These values were used in place of $\Delta\Delta C_T$ values to determine the ratio of target sequences in the test and calibrator samples and to quantify *S. chartarum* conidia in the test samples as described above.

Air sampling was performed in rooms that had previously been occupied by infants diagnosed with PH from three homes in the Cleveland, Ohio area. Airborne particles were recovered in sterile BioSampler® vials (SKC Inc., Eighty Four, Pa.) connected to an AirCon-2 High Flow Sampler pump (Gilian Instrument Co., Clearwater, Fla.). Air samples were taken over an eight hour time period under passive conditions (i.e. with no activity occurring in the rooms) at a flow rate of 10 liter per min., for a total collection volume of 4.8 m³. Two additional air samples were taken in the same manner over a twelve hour period from the basement of a home in the Cincinnati, Ohio area that was also determined to contain extensive *S. chartarum* growth. One of these samples was collected under passive conditions, as described above, while the other was collected under aggressive sampling conditions (i.e. during and after a cleaning effort in the contaminated area).

Each of the BioSampler vessels was rinsed three times with 5 ml of sterile water. The pooled rinses from each vial were transferred to sterile 50 ml capped test tubes (25330–50; Corning Inc., Corning, N.Y.) and centrifuged for 15 min at 1,000×g in a Sorval RC2 centrifuge using the SS-34 rotor (DuPont Instruments, Newton, Conn.). After carefully pipeting off the top 13 to 14 ml of the supernatants, the pelleted materials in each tube were resuspended in the remaining liquid and transferred to 2 ml microfuge tubes (16-8100-27; PGC Scientific, Frederick, Md.). These suspensions were centrifuged at 14,000 rpm for 3 min in an Eppendorf micro-centrifuge (5415C; Brinkman Instruments, Westbury, N.Y.) and the majority of the supernatants were again removed by pipetting. The pellets and small amounts of liquid remaining in each tube were adjusted to either to 100 or 200 μl with sterile water.

Direct counts of putative *S. chartarum* conidia in 10 μl aliquots of the recovered samples were made in a hemocytometer chamber. Separate counts of up to six separate aliquots of each sample were taken over the entire grid portion of the chamber and the mean counts were converted to cell concentrations based on the instrument manufacturer's specified total volume of this portion of the chamber. Presumptive identification and scoring of particles as *S. chartarum* conidia were based on recognition of the characteristic size, shape and pigmentation of these conidia. Three additional 10 μl aliquots of each recovered sample were mixed with *G. candidum* reference conidia and subjected to total genomic DNA extraction for subsequent analysis in the model 7700 as specified above.

Yields of target sequences extracted from these conidia samples and from calibrator samples were determined from their respective $C_T$ results in the model 7700 and compared using both the $\Delta\Delta C_T$ (including Geotrichum reference sequence data) and $\Delta C_{T,STAC}$ (not including reference sequence data) versions of the comparative $C_T$ method. Quantities of conidia estimated from these analyses were then compared with those determined from direct microscopic counts of the samples taken in a hemocytometer.

Results obtained by the $\Delta C_{T,STAC}$ analysis method and from direct counting showed good agreement for most of the samples (Example 1, FIG. 1). In thirteen of these fourteen instances, the estimate of the $\Delta C_{T,STAC}$ method was within a 1-fold range of the direct counting result. The results further indicated that this level of presumed accuracy and precision (i.e. within a 50–200% range of direct counts) may be expected to occur in 95% of all analyses performed by the $\Delta C_{T,STAC}$ method. Based on comparisons of results obtained by the $\Delta\Delta C_T$ analysis method for the same samples (data not shown), it was estimated that this method would provide the same level of accuracy in only about 70% of all analyses. Conidia from each of the different strains examined appeared to be quantified with similar degrees of precision and accuracy using the $\Delta C_{T,STAC}$ analysis method.

Figure 2:
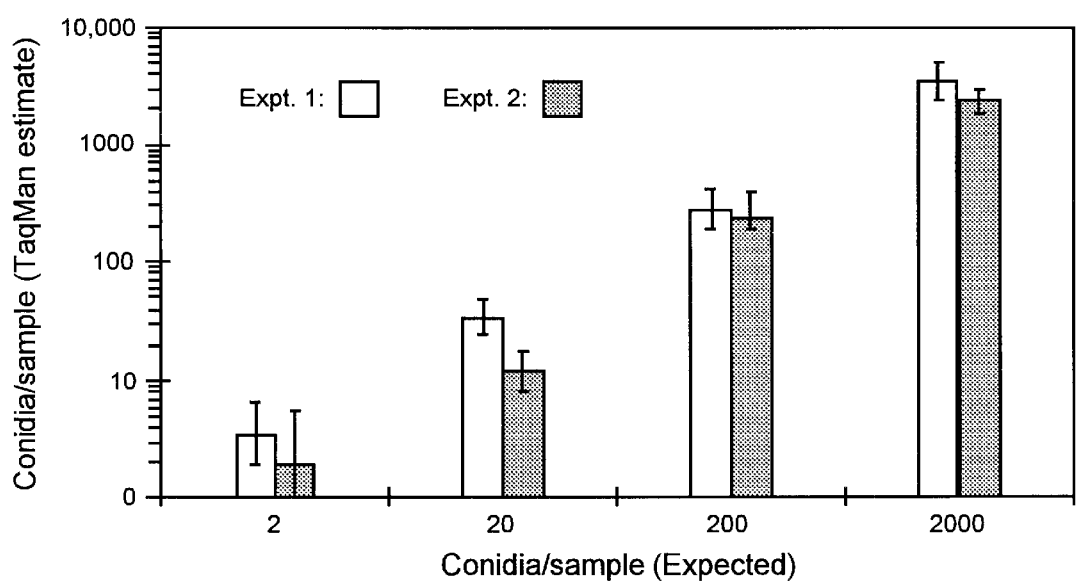
FIG. 2 shows the actual vs. the expected amounts of conidia detected.
Figure 3:
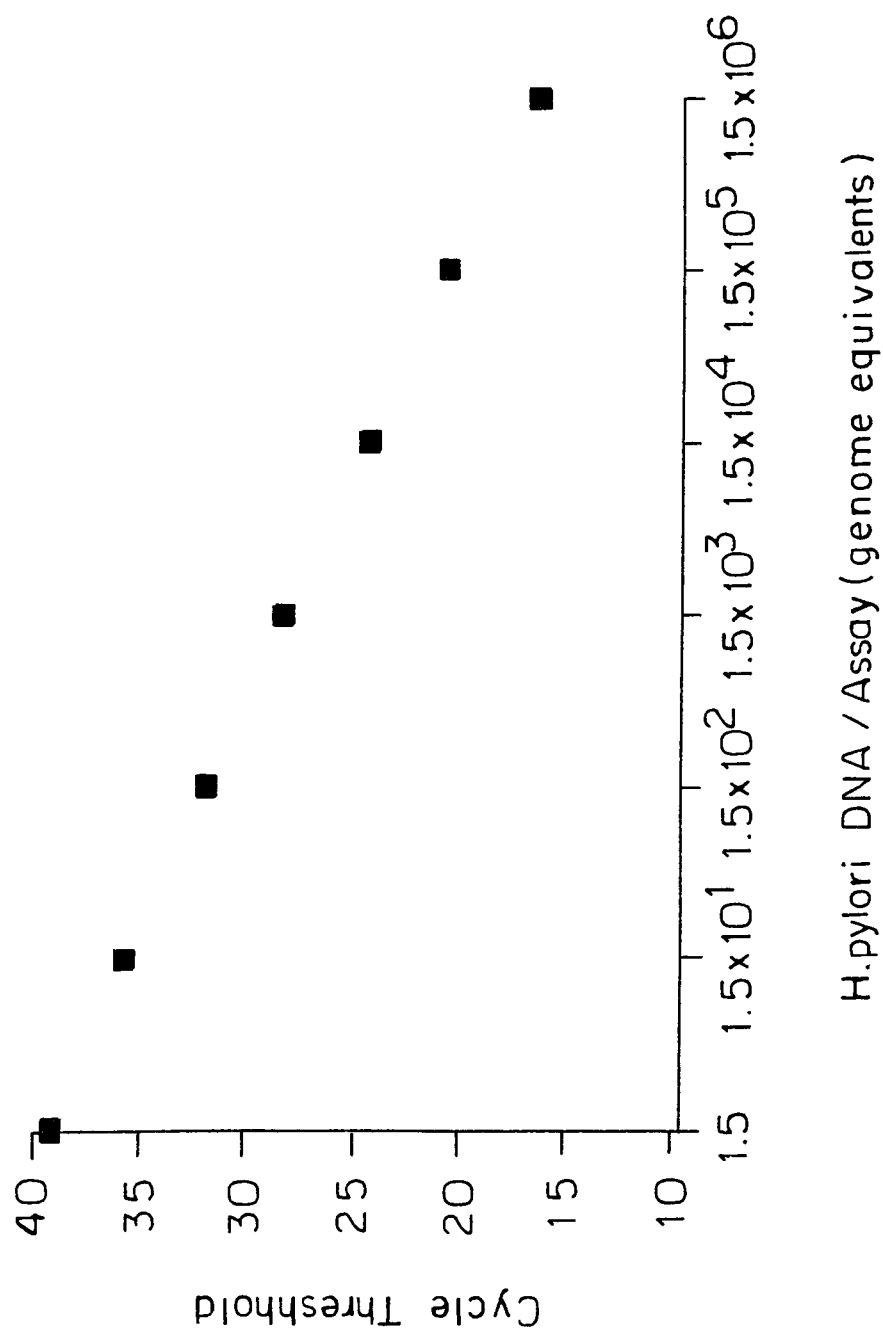
FIG. 3 shows TaqMan Threshold Responses from ten-fold dilutions of a single DNA extract.

The sensitivity of the TaqMan assay and the functional dynamic range of the $\Delta C_{T,STAC}$ quantitation method were further examined using ten-fold serial dilutions of *S. chartarum* strain UMAH 6417 conidia stock suspensions as test samples. These samples contained expected quantities of cells that ranged from 2 to 2000, based on direct counting analyses of the starting stock suspensions. The results of these analyses were again in good agreement with the expected results (Example 1, FIG. 2). Five of the eight measurements gave estimates that coincided with the expected quantities of conidia in the samples within the relative errors of the analyses. The mean results of these analyses were within a 1-fold range of the expected values in all instances. In one of these two experiments, a low level of signal (equivalent to an estimated mean quantity of 0.27 conidia) was observed in the negative control samples. Parallel samples taken from one of the two dilution series of conidia (cf. experiment 2 in Example 1, FIG. 2) were also subjected to DNA extractions in the absence of Geotrichum cells. Although these extracts yielded slightly lower quantitative results than those obtained for the corresponding samples extracted with the normal amendment of Geotrichum cells, the difference in results was not statistically significant (p=0.35>0.05, data not shown).

A final evaluation of the TaqMan assay and $\Delta C_{T,STAC}$ method was made by analyzing particulate samples collected from the inside air of four homes with known colonization by *S. chartarum*. TaqMan-based results were again compared with those obtained by direct microscopic observations of the samples in a hemocytometer. The two methods again gave similar mean determinations of the quantities of *S. chartarum* conidia in these samples with four of the five results agreeing within the relative errors of the TaqMan analyses (Example 1, Table 1). No *S. chartarum* conidia were found in the fifth sample by direct microscopic observation, however, this sample also appeared to approach the detection limits of the TaqMan assay with only two of the three replicate DNA extracts producing signals above background.

Example 1, Table 1. Quantification of *S. chartarum* conidia recovered from indoor air samples by direct microscopic counting and the $\Delta C_{T,STAC}$ method as determined from TaqMan analysis.

TABLE 1

Quantification of *S. chartarum* conidia recovered from indoor air samples by direct microscopic counting and the $\Delta C_{T,STAC}$ method as determined from TaqMan analysis.

| Sample Source | Sampling Conditions[a] | Direct Count Estimate Conidia/m³ air | $\Delta C_{T,STAC}$ TaqMan Estimate Conidia/m³ air | Relative error |
|---|---|---|---|---|
| Home 1[b] | Passive | 46[c] | 23[b] | 7.5–69 |
| Home 2[b] | Passive | 15[c] | 14[c] | 5.2–37 |
| Home 3[b] | Passive | 31[c] | 26[c] | 9.4–68 |
| Home 4[d] | Passive | 0[e] | 2.2[e] | 0.3–19 |
| Home 4[d] | Aggressive | 5600[e] | 4300[e] | 2600–7300 |

[a] Defined in materials and methods
[b] Located in Cleveland, Ohio
[c] Value based on a total air sample volume of 4.8 m³
[d] Located in Cincinnati, Ohio
[e] Value based on a total air sample volume of 7.2 m³

Example 2
Quantification of Fungus From Dust Using Real Time, Fluorescent Probe-Based Detection of PCR Products Dust samples from the home of an infant with pulmonary hemosiderosis in Cleveland, Ohio (Home 1) were collected using 37-mm filter cassettes, pore size 0.8 µm, as the collection device. Samples were obtained from two rooms in the basement, the living room, and the dining room. Additional dust samples were obtained in a similar manner from the basement of a home in Cincinnati, Ohio (Home 2) containing a significant, but localized, growth of *S. chartarum* as determined by surface sample analysis. One sample was taken from the floor directly beneath the area of growth, a second from another location in the same room and a third from an adjacent room in the basement. All of these dust samples were sieved through a 75 µm mesh and stored in a −20° C. freezer.

Total DNAs were extracted from dust samples using glass bead milling and glass milk adsorption method. Weighed dust samples were added directly to sterile 2 ml conical bottom, screw cap tubes (506–636; PGC Scientifics, Gaithersburg, Md.), containing 0.3 g of glass beads (G-1277; Sigma, St. Louis, Mo.) and 100 and 300 µl of lysis and binding buffer, respectively from an Elu-Quik DNA Purification Kit (Schleicher and Schuell, Keene, N.H.). Ten µl aliquots of a $2 \times 10^7$ conidia/ml suspension of *G. candidum* in 0.5% Tween 20 were also routinely added to the tubes as a potential source of reference DNA sequences. Ten µl aliquots of *S. chartarum* conidia suspensions in water were also added as needed. The tubes were shaken in a mini beadbeater (Biospec Products, Bartlesville, Ohio) for one minute at a maximum speed. To bind the DNA, 25 µl of Elu-Quik glass milk suspension (Schleicher and Schuell, Keene, HN) was added to the samples and the tubes were placed on a mini-rotating mixer (Glas-Col, Terre Haute, Ind.) for 20 minutes. The samples were transferred to SPIN™ filter and catch tube assemblies (BIO 101, Vista Calif.) and centrifugation at 7500×g for 1.5 min to remove binding and lysis buffers. The retained particulates, including glass milk with adsorbed nucleic acids, were washed twice in the filter cartridges with 0.5 ml Elu-Quik wash buffer and once with 0.5 ml Elu-Quik salt reduction buffer and centrifuged as above after each wash. Nucleic acids were desorbed from the glass milk particles by two successive washes with 100 µl distilled water and collected by centrifuging the washes into clean catch tubes. Calibrator samples, used in the analytical method as standards for the quantification of *S. chartarum* conidia in the test samples, contained $2 \times 10^4$ *S. chartarum* and $2 \times 10^5$ *G. candidum* conidia with no dust and DNA extractions from these samples was performed in the same manner.

PCR reactions were prepared in 0.5 ml thin-walled, optical grade PCR tubes (PE Biosystems, Foster City Calif.). Each reaction contained 12.5 µl of "Universal Master Mix"- a 2×concentrated, proprietary mixture of AmpliTaq Gold™ DNA polymerase, AmpErase® UNG, dNTPs, passive reference dye and optimized buffer components. (PE Biosystems, Foster City Calif.), 0.5 µl of a mixture of forward and reverse primers at 50 mM each, 2.5 µl of 400 nM TaqMan probe (PE Biosystems, Foster City, Calif.), 2.5 µl of 2 mg/ml fraction V bovine serum albumin (Sigma Chemical, St. Louis, Mo.) and 2 µl of autoclaved water. Five µl of purified DNA extract was added to complete the 25 µl reaction mix.

The TaqMan probes and primers were obtained from the custom oligonucleotide synthesis facility at PE-Applied Biosystems (Foster City, Calif.). TaqMan probes contained a TAMRA group conjugated to their 3'-terminal nucleotide and a FAM group linked to their 5'-terminal nucleotides as the quencher and reporter fluorochromes, respectively. For *Geotrichum candidum*, the forward primer is NS92F: 5'-CACCGCCCGTCGCTAC (SEQ ID NO:86), the reverse primer is GcandR1: 5'-AGAAAAMAAGTTGCCCTCTCCAGTT (SEQ ID NO:87), and the probe is GeoP2: 5'-TCAATCCGGAAGCCTCACTAAGCCATT (SEQ ID NO:88). For *Stachybotrys chartarum*, the forward primer is StacF4 5'-TCCCAAACCCTTATGTGAACC (SEQ ID NO:186), the reverse primer is StacR5 5'-GTTTGCCACTCAGAGAATACTGAAA (SEQ ID NO:187), and the probe is StacP2 5'-CTGCGCCCGGATCCAGGC (SEQ ID NO;188).

Standard procedures for the operation of the model 7700, as described in the instrument's manual, were followed using all of the default program settings with the exception of reaction volume which was changed from 50 to 25 µl. Thermal cycling conditions consisted of 2 minutes at 50° C., 10 minutes at 95° C., followed by 40 cycles of 15 seconds at 95° C. and 1 minute at 60° C. Cycle threshold ($C_T$) determinations were automatically performed by the instrument for each assay using default parameters. Assays for *S. chartarum* sequences and *G. candidum* sequences in the same DNA samples were performed in separate reaction tubes.

To quantify conidia the mean *S. chartarum* calibrator $C_T$ value was subtracted from the mean *S. chartarum* sequence $C_T$ values in the sample extracts to obtain $\Delta C_{T,STAC}$ values. Ratios of target sequences in the test and calibrator samples were multiplied by the known quantities of S. chartarum conidia in the calibrator samples to obtain measurements of the quantities of these conidia in the test samples. similar calculations were performed in parallel using G. candidum sequence $C_T$ values from the same calibrator and test samples to determine $\Delta C_{T,GEO}$ values and quantities of these conidia in the test samples.

Then G. candidum sequence $C_T$ values were subtracted from mean S. chartarum sequence $C_T$ values for both test and calibrator sample extracts to obtain $\Delta C_T$ values. Calibrator sample $\Delta C_T$ values were then subtracted from the test sample $\Delta C_T$ values to obtain $\Delta\Delta C_T$ values. These values were used in place of $\Delta C_{T,STAC}$ values to determine the ratios of S. chartarum target sequences in the test and calibrator samples and to quantify S. chartarum conidia in the test samples as indicated above.

Variances of $\Delta C_T$ were estimated from the results of the replicate extracts of each sample by: $S_{\Delta C_T}^2 = S_{Target}^2 + S_{Ref}^2 - 2rS_{Target}S_{Ref}[1]$, where $S_{Target}$ and $S_{Ref}$ are the standard deviations (SD) of the S. chartarum and G. candidum assay results, respectively, and r is the correlation coefficient between these results. Variances of $\Delta\Delta C_T$ were estimated by $S_{\Delta\Delta C_T}^2 = S_{\Delta C_T(C)}^2 + S_{\Delta C_T(S)}^2[2]$, where $S_{\Delta CT(C)}$ is given by Equation [1] applied to the calibrator results, and $S_{\Delta CT(S)}$, by Equation [1] applied to the test sample results. Since calibrator and test sample $C_T$ values were independent of one another; variances of $\Delta C_{T,STAC}$ results were estimated by: $S_{\Delta C_{T,STAC}}^2 = S_{Calib}^2 + S_{Target}^2[2]$, where $S_{Calib}$ was the SD of the $C_T$ for the calibrator. Variances of $\Delta C_{T,GEO}$ values were calculated in the same manner. Standard errors of difference were determined from the appropriate standard deviation divided by the square root of the number of replicate observations (extractions), and confidence intervals for the differences were constructed using these standard errors.

With $N_0$ representing the number of cells in the calibrator sample, the corresponding cell numbers in test samples were estimated by $N_0 2^{-\Delta Y}[4]$, where $\Delta Y$ was the estimator $\Delta\Delta C_T$, $\Delta C_{T,STAC}$, or $\Delta C_{T,GEO}$. In this paper the term "relative error" refers the range implied by one standard deviation about $\Delta Y$, i.e. $N_0 2^{-\Delta Y \pm S_{\Delta Y}}$, in which $S_{\Delta Y}$ is given by equation [2] or [3]. Confidence intervals were constructed around the estimated cell numbers by $N_0 2^{-\Delta Y \pm t \cdot S_{\Delta Y}/\sqrt{3}}$, where t is the appropriate Student t-value and three replicate extractions were used.

In method evaluation experiments, conidia quantities determined by the $\Delta\Delta C_T$, $\Delta C_{T,STAC}$, or $\Delta C_{T,GEO}$ methods ($N_T$) were compared to "known" quantities of conidia added to the dust samples. The "known" quantities were determined from hemocytometer cell counts of three replicate aliquots (at least 400 total counts) of the conidia stock suspensions used for dilution and sample amendment. The "known" value for $\Delta C_T$ ($N_H$) was calculated from equation [4] based on the hemocytometer counts and dilution factors, and the differences: d=$\Delta C_T$-known value were evaluated via analysis of variance to test the null hypothesis: d=0. The 95% confidence level range for individual observations of d was constructed, assuming d to be normally distributed, and used to characterize the precision of a single estimate utilizing TaqMan quantification. Note that when antilogs are taken, the confidence interval describes lower and upper limits to the ratio $N_T/N_H$.

The direct enumeration of Stachybotrys conidia in dust samples was performed by weighing dust samples, suspending them in 0.5% Tween 20 to a concentration of 1 mg/ml and, with constant mixing of the suspensions, aliquots were applied to a hemocytometer chamber. Nine replicate aliquots, or fewer if this was sufficient to enumerate at least 400 conidia, were counted in this manner for each suspension. The volumes of the examined grids were used to calculate conidia numbers per ml of suspension and these values converted to numbers per mg of dust. For comparability with relative error of the TaqMan estimates, one standard deviation ranges for direct count estimates were calculated. Conidia were assumed to be randomly distributed within each grid. Under this assumption the corresponding relative error is a range such that the observed count represents an observation one standard deviation above or one standard deviation below a Poisson variable with mean given by the lower or upper limit, respectively.

Quantitative measurements of S. chartarum conidia in dust samples taken from two contaminated homes were obtained by $\Delta\Delta C_T$ analyses of TaqMan assay results and compared with the results of presumptive direct microscopic enumeration of these conidia. Mean estimates obtained from the TaqMan assays fell within, or very close to the 0.24 to 1.04 range of direct counts that was predicted by the method evaluation experiments (Example 2, Table 1).

TABLE 1

Quantities of S. chartarum conidia in home dust samples determined by $\Delta\Delta C_T$ TaqMan analysis and direct microscopic enumeration.

| Location in Home | Proximity to Fungal Growth | $\Delta\Delta CT$ TaqMan Estimate Conidia/5 mg dust | Relative Error[g] | Direct count estimate Conidia/5 mg dust | Relative Error[g] |
|---|---|---|---|---|---|
| Living Rm | Remote Room[d] | 6 | 4–10 | 667 | 444–1000 |
| Basement | Same Room | 1100[f] | — | 2333 | 1877–2901 |
| Basement | Same Room | 9200 | 7100–12000 | 26889 | 25215–28674 |
| Dining Rm | Remote Room | 560 | 420–740 | 1444 | 1096–1904 |
| Basement | Same Room | 23800 | 18300–31000 | 30444 | 28660–32340 |
| Basement | Adjacent Room | 300 | 260–340 | 778 | 534–1133 |
| Basement | Same Room[e] | 77200 | 56700–105000 | 68286 | 50737–55597 |
| HVAC | | 1.7 | 0.3–11.2 | 556 | 357–866 |

[a]Home 1 located in Cleveland, Ohio
[b]Home 2 located in Cincinnati, Ohio
[c]Composite HVAC system dust as described in Methods section of text
[d]Small amount of fungal growth, no confirmed Stachybotrys
[e]Sample collected directly beneath area of fungal growth Analyses of known numbers of Stachybotrys conidia over a range from $2 \times 10^1$ to $2 \times 10^4$ in the presence of 10 mg of composite HVAC system dust were found to provide 95% occurrence results within a range from 25% to 104% of expected values using this approach.

A second type of matrix effect that can affect PCR-based analyses of dust samples is the influence of PCR inhibitory compounds. Retention of such compounds through the DNA extraction and purification procedures occurred in only one sample in this study. A simple procedure, involving the dilution and re-analysis of a DNA extract from this sample was used to identify this matrix effect and to obtain a corrected estimate of conidia quantities. This procedure should be generally applicable so long as the concentrations of target sequences in the samples are sufficiently high to still be detectable after the inhibitor's effects are negated by dilution. In practice, however, such follow-up analyses are only likely to be necessary when significant differences are observed in the reference sequence assay results of test and calibrator samples in the initial analyses of the samples.

Example 3

Evaluation of *Stachybotrys chartarum* in the House of an Infant with Pulmonary Hemorrhage: Quantitative Assessment Before, During and After Remediation Air samples (Example 3, Table 1) were taken in a home under remediation for mold damage in two ways; either using a cassette filter (37 mm with 0.8 mm filter) or with a BioSampler (SKC, Eighty Four, Pa.) connecting to an AirCon-2 High Flow Sampler pump (Gilian Instrument Co., Clearwater, Fla.) calibrated at a flow rate of 10 liter per min. These samples were taken for a period between 6 and 90 hrs at 10 liter per min (L/min). During the remediation process itself, one of the workers wore a personal monitoring pump (PMP) for about 6 h a day which also used a cassette filter (37 mm with 0.8 mm filter).

Conidial stocks of the target fungus, i.e. *Stachybotrys chartarum*, and the reference target, i. e. *Geotrichum candidum*, were prepared to act as calibrator and internal standard, respectively.

Genomic DNAs were extracted from 20 μl conidial suspensions using a glass bead milling and glass milk adsorption method. Briefly, this method involved mixing test and reference conidia suspensions (10 μl ea.) with 0.3 g of acid-washed glass beads (G-1277; Sigma, St. Louis, Mo.) and 10 μl, 100 μl and 300 μl, respectively, of glass milk suspension, lysis buffer and binding buffer from an Elu-Quik DNA purification kit (Schleicher and Schuell, Keene, N.H.) in sterile 2 ml conical bottom, screw cap tubes (506–636; PGC Scientifics, Gaithersburg, Md.). The tubes were shaken in a mini beadbeater (Biospec Products, Bartlesville, Okla.) for one minute at maximum rate and DNAs were recovered in final volumes of 200 μl distilled water after performing a slight modification of the small-scale protocol provided with the Elu-Quik purification kit.

The TaqMan probes and primers were obtained from the custom oligonucleotide synthesis facility at PE-Applied Biosystems (Foster City, Calif.). TaqMan probes contained a TAMRA group conjugated to their 3'-terminal nucleotide and a FAM group linked to their 5'-terminal nucleotides as the quencher and reporter fluorochromes, respectively. For *Geotrichum candidum*, the forward primer is NS92F: 5'-CACCGCCCGTCGCTAC (SEQ ID NO:86), the reverse primer is GcandR1: 5'-AGAAAAGTTGCCCTCCAGTT (SEQ ID NO:87), and the probe is GeoP2: 5'-TCAATCCGGAAGCCTCACTAAGCCATT (SEQ ID NO:88). For *Stachybotrys chartarum*, the forward primer is StacF4 5'-TCCCAAACCCTTATGTGAACC (SEQ ID NO:186), the reverse primer is StacR5 5'-GTTTGCCACTCAGAGAATACTGAAA (SEQ ID NO:187), and the probe is StacP2 5'-CTGCGCCCGGATCCAGGC (SEQ ID NO:188).

PCR reactions were prepared in 0.5 ml thin-walled, optical grade PCR tubes (PE Applied Biosystems, Foster City Calif.) by addition of the following components: 12.5 μl of TaqMan Universal Master Mix, a 2×concentrated, proprietary mixture of AmpliTaq Gold™ DNA polymerase, AmpErase® UNG, dNTPs with UTP, passive reference dye and optimized buffer components (PE Applied Biosystems, Foster City Calif.); 2.5 μl of a mixture of forward and reverse primers (10 nM each); 2.5 μl of 400 nM TaqMan probe; 2.5 μl of 2 mg/ml bovine serum albumin (fraction V, Sigma Chemical, St. Louis, Mo.) and 5 μl of DNA template. Standard procedures for the operation of the model 7700, as described in the instrument's manual, were followed. This included the use of all default program settings with the exception of reaction volume which was changed from 50 to 25 μl. Thermal cycling conditions consisting of two min at 50° C., 10 min at 95° C., followed by 40 cycles of 15 sec at 95° C. and 1 min at 60° C. Cycle threshold ($C_T$) determinations, i.e. non-integer calculations of the number of cycles required for reporter dye fluorescence resulting from the synthesis of PCR products to become significantly higher than background fluorescence levels were automatically performed by the instrument for each reaction using default parameters. Assays for *S. chartarum* (target) sequences and *G. candidum* (reference) sequences in the same DNA samples were performed in separate reaction tubes.

Results of air sampling with either filters or BioSamplers indicated that the number of airborne *S. chartarum* spores in this PH house was low before the remediation began (Example 3, Table 1). The number of *S. chartarum* spores in the air, when the furnace blower was activated (typical condition for the winter months), increased by a factor of 17–47 in the living room. During demolition, the number of *S. chartarum* spores in the air increased by four orders of magnitude in the basement, about three orders of magnitude in the dining room and about two orders of magnitude in the upstairs bedroom (Example 3, Table 1). Thus this technology, under actual conditions, can detect the target fungus over four orders of magnitude.

TABLE 1

Results of air sampling for *S. chartarum* (S.c.) spores in the mold contaminated home.

| Date | Sample Method | Location (Room = RM) | Sampling Time (H) | S.c. Spores (#/m³ air) |
|---|---|---|---|---|
| Pre-remediation | | | | |
| 12/29–30 | Filter (passive)[1] | Living Rm | 25.5 | 0.2 |
| | BioSampler (passive) | Living Rm | 25.5 | 0.3 |
| 12/30–31 | Filter (active)[2] | Living Rm | 24 | 9.3 |
| | BioSampler (active) | Living Rm | 24 | 5.0 |
| 12/31 | Filter (active) | Dining Rm | 90 | 0.1 |
| | Biosampler (active) | Dining rm | 90 | 1.7 |
| 12/31–1/4 | Filter (active) | Basement | 90 | 0.6 |
| During Remediation[3] | | | | |
| 1–19 | Filter | Basement | 6.6 | $1.1 \times 10^3$ |
| | Biosampler | Basement | 6.6 | $1.6 \times 10^3$ |
| | Filter PMP[4] | Basement | 6.5 | $2.0 \times 10^3$ |

TABLE 1-continued

Results of air sampling for *S. chartarum* (S.c.) spores in the mold contaminated home.

| Date | Sample Method | Location (Room = RM) | Sampling Time (H) | S.c. Spores (#/m³ air) |
|---|---|---|---|---|
| 1–20 | Filter | Dining Rm | 6.25 | $1.8 \times 10^3$ |
|  | BioSampler | Dining Rm | 6.25 | $2.7 \times 10^3$ |
|  | Filter PMP | Dining Rm | 5.75 | $4.0 \times 10^3$ |
| 1–21 | Filter | N. Bedrm | 7.75 | $0.1 \times 10^3$ |
|  | BioSampler | N. Bedrm | 7.75 | $0.1 \times 10^3$ |

[1]"passive" means furnace blower off, furnace sealed and inoperable.
[2]"active" means furnace blower on, furnace operable.

Example 4
Identification and Quantification of *Helicobacter pylori*

Culturing of *Helicobacter pylori* from environmental sources continues to be an obstacle in detecting and enumerating this organism. Selection of primer and probe sequences for the ureA gene was performed based on comparative sequence analyses of 16 strains of *H. pylori* and other Helicobacter species. For *Helicobacter pylorii*, the forward primer is Hpy1F1: 5'-GGGTATTGAAGCGATGTTTCCT (SEQ ID NO:223), the reverse primer is Hpy1R1: 5'-GCTTTTTTGCCTTCGTTGATAGT (SEQ ID NO:224), and the probe is Hpy1R1: 5'-AAACTCGTAACCGTGCATACCCCTATTGAG (SEQ ID NO:225).

DNA was extracted from aliquots of ten-fold serial dilutions of *H. pylori* by EluQuick kits from Schleeicher and Schuell, Inc. The cells were lysed, DNA bound to glass beads and washed with alcohol and salt reduction solutions followed by elution from filters with water. One set of extraction tubes contained only *H. pylori*. A second set also received $10^7$/ml *E. coli*. Portions of some DNA extracts were subjected to agarose gel electrophoresis and GelStar staining. Yields of high molecular weight total DNA (appearing as bands on the 1.5% gels) were estimated by comparisons of their fluorescence signals with those of a series of known mass standards (Gibco/BRL) using a model S1 fluorimager (Molecular Dynamics).

The more commonly identified non-pylori Helicobacter species were tested with *H. pylori* primers and probe (Example 4, Table 1). Results show that when compared to the negative extraction control all of these species were also negative. All obtained $C_T$ values in the range of 37 to 39. A 40 $C_T$ is the lowest negative value obtainable. Counts of the bacteria were high. They ranged from $10^7$ to $10^8$ per assay. The *H. pylori* strain also was initially in this range with a $C_T$ value was 15.

TABLE 1

| Bacteria | Dilution | Cells/TaqMan | $C_T$ Values |
|---|---|---|---|
| *Campylobacter jejuni* | $10^0$ | $8.75 \times 10^6$ | 36.55 |
|  | $10^{-1}$ | $8.75 \times 10^5$ | 36.86 |
|  | $10^{-2}$ | $8.75 \times 10^4$ | 38.78 |
| *Helicobacter felis* | $10^0$ | $6.8 \times 10^5$ | 37.55 |
|  | $10^{-1}$ | $6.8 \times 10^4$ | 36.17 |
|  | $10^{-2}$ | $6.8 \times 10^3$ | 38.21 |
| *Helicobacter hepaticus* | $10^0$ | $2.3 \times 10^7$ | 36.68 |
|  | $10^{-1}$ | $2.3 \times 10^6$ | 37.14 |
|  | $10^{-2}$ | $2.3 \times 10^5$ | 39.74 |

TABLE 1-continued

| Bacteria | Dilution | Cells/TaqMan | $C_T$ Values |
|---|---|---|---|
| *Helicobacter mustelae* | $10^0$ | $1.9 \times 10^8$ | 34.66 |
|  | $10^{-1}$ | $1.9 \times 10^7$ | 36.37 |
|  | $10^{-2}$ | $1.9 \times 10^6$ | 37.65 |
| *Helicobacter pylori* | $10^0$ | $2.1 \times 10^7$ | 14.93 |
|  | $10^{-1}$ | $2.1 \times 10^6$ | 18.23 |
|  | $10^{-2}$ | $2.1 \times 10^5$ | 21.45 |
|  | $10^{-3}$ | $2.1 \times 10^4$ | 25.24 |
|  | $10^{-4}$ | $2.1 \times 10^3$ | 32.73 |
|  | $10^{-5}$ | $2.1 \times 10^2$ | 34.63 |
|  | $10^{-6}$ | $2.1 \times 10^1$ | 35.24 |
|  | $10^{-7}$ | $2.1 \times 10^0$ | 39.58 |
| Negative Extraction Control | — | — | 37.65 |
| Positive Calibrator Control | $10^{-1}$ | $9.8 \times 10^5$ | 17.3 |

Samples of serially diluted *H. pylori* cells spanning a 6-log concentration range were subjected to DNA extraction and TaqMan analysis.

Estimated cell quantities in the extracted samples ranged from 20 to $2 \times 10^6$ based on direct microscopic counts following staining with DAPI. Results from 5 replicate experiments showed a good correlation (r2=0.99) between TaqMan assay results (expressed as cycle threshold values) and the logarithms of expected cell numbers based on direct counts over the entire cell quantity range tested. Similar results were seen for two Helicobacter pylori strains. It was concluded that the TaqMan quantitative PCR method has the potential to provide accurate quantification of *H. pylori* cells in environmental samples.

Ten-fold dilutions of a single DNA extract are shown in FIG. 4 along with the corresponding regression analysis. This curve is linear all the way to a negative $C_T$ of 40. The R-squared is 0.999. Counts that correspond to the initial dilution can be extrapolated for the other dilutions and can be included on the X-axis. FIG. 4 shows a linear range from $1.5 \times 10^5$ to 1.5 genome equivalents.

Example 4, FIG. 4. Log (base 10)*H. pylori* counts per assay are plotted against the cycle threshold values.

Conclusions

Having now fully described this invention, it will be appreciated by those skilled in the art that the same can be performed within a wide range of equivalent parameters, concentrations, and conditions without departing form the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the intention and including such departures from the present disclosure as come within known or customary practice within the art to which the invention pertains and as may be applied to the essential features hereinbefore set forth as follows in the scope of the appended claims.

REFERENCES

Haugland, R. A. and Heckman J. L. 1998. Identification of putative sequence specific PCR primers for detection of the toxigenic fungal species *Stachybotrys chartarum*. Molec. Cellular Probes. 12:387–396.

Haugland, R. A, J. L. Heckman, and L. J. Wymer. 1999. Evaluation of different methods for the extraction of DNA from fungal conidia by quantitative competitive PCR. J. Microbiol. Methods. 37:165–176.

Haugland, Vesper, Wymer. 1999. Quantitative Measurement of *Stachybotrys chartarum* conidia Using Real Time Detection of PCR Products with the TaqMan™ Fluorogenic Probe System. Molecular and Cellular Probes. Molecular and Cellular Probes. 13:332–340.

Vesper, Dearborn, Yike, Allan, Sobolewski, Hinkley, Jarvis, Haugland. 2000. Evaluation of *Stachybotrys chartarum* in the House of an Infant with Pulmonary Hemorrhage: Quantitative Assessment Before, During and After Remediation. Journal of Urban Health. 77:68–85.

What is claimed is:

1. A method for detecting and quantifying specific fungi or bacteria in a sample comprising:
   a. extracting and recovering DNA from the organism in the sample;
   b. hybridizing and amplifying the DNA sequences such that the specific fungus or bacterium can be identified and quantified without interference from DNA in the sample belonging to other fungi or bacteria.

2. The method according to claim 1 wherein the fungi and bacteria are selected from the group consisting of Absidia coerulea, Absidia glauca, Absidia corymbifera, Acremonium strictum, Alternaria alternata, Apophysomyces elegans, Saksena vasiformis, Aspergillus flavus, Aspergillus oryzae, Aspergillus fumigatus, Neosartoryta fischeri, Aspergillus niger, Aspergillus foetidus, Aspergillus phoenicus, Aspergillus nomius, Aspergillus ochraceus, Aspergillus ostianus, Aspergillus auricomus, Aspergillus parasiticus, Aspergillus sojae, Aspergillus restrictus, Aspergillus caesillus, Aspergillus conicus, Aspergillus sydowii, Aspergillus tamarii, Aspergillus terreus, Aspergillus ustus, Aspergillus versicolor, Aspergillus ustus, Aspergillus versicolor, Chaetomium globosum, Cladosporium cladosporioides, Cladosporium herbarum, Cladosporium sphaerospermum, Conidiobolus coronatus, Conidiobolus incongruus, Cunninghamella elegans, Emericella nidulans, Emericella rugulosa, Emericilla quadrilineata, Apicoccum nigrum, Eurotium amstelodami, Eurotium chevalieri, Eurotium herbariorum, Eurotium rubrum, Eurotium repens, Geotrichum candidum strain UAMH 7863, Geotrichum candidum, Geotrichum klebahnii, Memnoniella echinata, Mortierella polycephala, Mortierella wolfii, Mucor mucedo, Mucor amphibiorum, Mucor circinelloides, Mucor heimalis, Mucor indicus, Mucor racemosus, Mucor ramosissimus, Rhizopus azygosporous, Rhizopus homothalicus, Rhizopus microsporus, Rhizopus oligosporus, Rhizopus oryzae, Myrothecium verrucaria, Myrothecium roridum, Paecilomyces lilacinus, Paecilomyces variotii, Penicillium freii, Penicillium verrucosum, Penicillium hirsutum, Penicillium alberechii, Penicillum aurantiogriseum, Penicillium polonicum, Penicillium viridicatum, Penicillium hirsutum, Penicillium brevicompactum, Penicillium chrysogenum, Penicillium griseofulvum, Penicillium glandicola, Penicillium coprophilum, Eupenicillium crustaceum, Eupenicillium egyptiacum, Penicillium crustosum, Penicillium citrinum, Penicillium sartoryi, Penicillium westlingi, Penicillium corylophilum, Penicillium decumbens, Penicillium echinulatum, Penicillium solitum, Penicillium camembertii, Penicillium commune, Penicillium echinulatum, Penicillium sclerotigenum, Penicillium italicum, Penicillium expansum, Penicillium fellutanum, Penicillium charlesii, Penicillium janthinellum, Penicillium raperi, Penicillium madriti, Penicillium gladioli, Penicillium oxalicum, Penicillium roquefortii, Penicillium simplicissimum, Penicillium ochrochloron, Penicillium spinulosum, Penicillium glabrum, Penicillum thomii, Penicillium pupurescens, Eupenicillium lapidosum, Rhizomucor miehei, Rhizomucor pusillus, Rhizomucor variabilis, Rhizopus stolonifer, Scopulariopsis asperula, Scopulariopsis brevicaulis, Scopulariopsis fusca, Scopulariopsis brumptii, Scopulariopsis chartarum, Scopulariopsis sphaerospora, Trichoderma asperellum, Trichoderma hamatum, Trichoderma viride, Trichoderma harzianum, Trichoderma longibrachiatum, Trichoderma citroviride, Trichoderma atroviride, Trichoderma koningii, Ulocladium atrum, Ulocladium chartarum, Ulocladium botrytis, Wallemia sebi, Escherichia coli, Helicobacter pylorii, Stachybotrys chartarum.

3. The method according to claim 2 wherein the fungi are selected from the group consisting of Absidia coerulea/glauca, the Forward Primer is NS92F: 5'-CACCGCCCGTCGCTAC (SEQ ID NO:1), the reverse primer is AcoerR1: 5'-TCTAGTTTGCCATAGTTCTCTTCCAG (SEQ ID NO:2), and the probe is MucP1: 5'-CCGATTGAATGGTTATAGTGAGCATATGGGATC (SEQ ID NO:3).

4. The method according to claim 2 wherein the fungi are selected from the group consisting of Absidia corymbifera, the forward primer is NS92F: 5'-CACCGCCCGTCGCTAC (SEQ ID NO:4), the reverse primer is AcoryR1: 5'-GCAAAGCGTTCCGAAGGACA (SEQ ID NO:5), and the probe is AcoryP1: 5'-ATGGCACGAGCAAGCATTAGGGACG (SEQ ID NO:6).

5. The method according to claim 2 wherein the fungi are selected from the group consisting of Acremonium strictum, the forward primer is AstrcF1: 5'-CAACCCATTGTGAACTTACCAAAC (SEQ ID NO:7), the reverse primer is AstrcR1: 5'-CGCCCCTCAGAGAAATACGATT (SEQ ID NO:8), and the probe is AstrcP1: 5'-TCAGCGCGCGGTGGCCTC (SEQ ID NO:9).

6. The method according to claim 2 wherein the fungi are selected from the group consisting of Alternaria alternata, the forward primer is AaltrF1: 5'-GGCGGGCTGGAACCTC (SEQ ID NO:10), the reverse primer is AltrR1-1: 5'-GCAATTACAAAAGGTTTATGTTTGTCGTA (SEQ ID NO:11), or the reverse primer is AaltrR1-2: 5'-TGCAATTACTAAAGGTTTATGTTTGTCGTA (SEQ ID NO:12), and the probe is AaltrP1: 5'-TTACAGCCTTGCTGAATTATTCACCCTTGTCTTT (SEQ ID NO:13).

7. The method according to claim 2 wherein the fungi are selected from the group consisting of Apophysomyces elegans and Saksenea vasiformis, the forward primer is NS92F: 5'-CACCGCCCGTCGCTAC (SEQ ID NO:14), the reverse primer is AelegR1: 5'-GACTCGAATGAGTTCTCGCTTC (SEQ ID NO:15), and the probe is AelegP1: 5'-TGGCCAAGACCAGAATATGGGATTGC (SEQ ID NO:16).

8. The method according to claim 2 wherein the fungi are selected from the group consisting of Aspergillus flavus/oryzae, the forward primer is AflavF1: 5'-CGAGTGTAGGGTTCCTAGCGA (SEQ ID NO:17), the reverse primer is AflavR1: 5'-CCGGCGGCCATGAAT (SEQ ID NO:18), and the probe is AflavP1: 5'-TCCCACCCGTGTTTACTGTACCTTAGTTGCT (SEQ ID NO:19).

9. The method according to claim 2 wherein the fungi are selected from the group consisting of Aspergillus fumigatus, Neosartorya fischeri, the forward primer is AfumiF1: 5'-GCCCGCCGTTTCGAC (SEQ ID NO:20), the reverse primer is AfumiR1: 5'-CCGTTGTTGAAAGTTTTAACTGATTAC (SEQ ID NO:21), and the probe is AfumiP1: 5'-CCCGCCGAAGACCCCAACATG (SEQ ID NO:22).

10. The method according to claim 2 wherein the fungi are selected from the group consisting of Aspergillus niger/foetidus/phoenicus, the forward primeris AnigrF1: 5'-GCCGGAGACCCCAACAC-3' (SEQ ID NO:23), the reverse primer is AnigrR1: 5'-TGTTGAAAGTTTTAACTGATTGCATT-3' (SEQ ID NO:24), and the probe is AnigrP1: 5'-AATCAACTCAGACTGCACGCTTTCAGACAG (SEQ ID NO:25).

11. The method according to claim 2 wherein the fungi are selected from the group consisting of *Aspergillus nomius*, the forward primer is AflavF1: 5'-CGAGTGTAGGGTTCCTAGCGA-3' (SEQ ID NO:26), the reverse primer is AnomiR1: 5'-CCGGCGGCCTTGC-3' (SEQ ID NO:27), and the probe is AflavP1: 5'-TCCCACCCGTGTTTACTGTACCTTAGTTGCT (SEQ ID NO:28).

12. The method according to claim 2 wherein the fungi are selected from the group consisting of *Aspergillus ochraceus/ostianus/auricomus*, the forward primer is AochrF1: 5'-AACCTCCCACCCGTGTATACC-3' (SEQ ID NO:29), the reverse primer is AochrR1: 5'-CCGGCGAGCGCTGTG-3' (SEQ ID NO:30), and the probe is AochrP1: 5-ACCTTGTTGCTTCGGCGAGCCC (SEQ ID NO:31).

13. The method according to claim 2 wherein the fungi are selected from the group consisting of *Aspergillus parasiticus/sojae*, the forward primer is AflavF1: 5'-CGAGTGTAGGGTTCCTAGCGA-3' (SEQ ID NO:32), the reverse primer is AparaR3: 5'-GCCCGGGGCTGACG-3' (SEQ ID NO:33), and the probe is AflavP1: 5'-TCCCACCCGTGTTTACTGTACCTTAGTTGCT (SEQ ID NO:34).

14. The method according to claim 2 wherein the fungi are selected from the group consisting of *Aspergillus restrictus/caesillus/conicus*, the forward primer is ArestF2: 5'-CGGGCCCGCCTTCAT-3' (SEQ ID NO:35), the reverse primer is ArestR1: 5'-GTTGTTGAAAGTTTTAACGATTTTTCT (SEQ ID NO:36), and the probe is ArestP1: 5'-CCCGCCGGAGACTCCAACATTG (SEQ ID NO:37).

15. The method according to claim 2 wherein the fungi are selected from the group consisting of *Aspergillus sydowii*, the forward primer is AsydoF1: 5'-CAACCTCCCACCCGTGAA-3' (SEQ ID NO:38), the reverse primer is versR1: 5'-CCATTGTTGAAAGTTTTGACTGATTTTA (SEQ ID NO:39), and the probe is versP1: 5'-AGACTGCATCACTCTCAGGCATGAAGTTCAG (SEQ ID NO:40).

16. The method according to claim 2 wherein the fungi are selected from the group consisting of *Aspergillus tamarii*, the forward primer is AflavF1: 5'-CGAGTGTAGGGTTCCTAGCGA (SEQ ID NO:41), the reverse primer is AtamaR1: 5'-CCCGGCGGCCTTAA (SEQ ID NO:42), and the probe is AflavP1: 5'-TCCCACCCGTGTTTACTGTACCTTAGTTGCT (SEQ ID NO:43).

17. The method according to claim 2 wherein the fungi are selected from the group consisting of *Aspergillus terreus*, the forward primer is AterrF1: 5'-TTACCGAGTGCGGGTCTTTA (SEQ ID NO:44), the reverse primer is AterrR1: 5'-CGGCGGCCAGCAAC (SEQ ID NO:45), and the probe is AterrP1: 5'-AACCTCCCACCCGTGACTATTGTACCTTG (SEQ ID NO:46).

18. The method according to claim 2 wherein the fungi are selected from the group consisting of *Aspergillus ustus*, the forward primer is AustsF1: 5'-GATCATTACCGAGTGCAGGTCT (SEQ ID NO:47), the reverse primer is AustsR1: 5'-GCCGAAGCAACGTTGGTC (SEQ ID NO:48), and the probe is AustsP1: 5'-CCCCCGGGCAGGCCTAACC (SEQ ID NO:49).

19. The method according to claim 2 wherein the fungi are selected from the group consisting of *Aspergillus versicolor*, the forward primer is AversF2: 5'-CGGCGGGGAGCCCT (SEQ ID NO:50), the reverse primer is versR1: 5'-CCATTGTTGAAAGTTTTGACTGATTTTA (SEQ ID NO:51), and the probe is versP1: 5'-AGACTGCATCACTCTCAGGCATGAAGTTCAG (SEQ ID NO:52).

20. The method according to claim 2 wherein the fungi are selected from the group consisting of *Chaetomium globosum*, the forward primer is CglobF1: 5'-CCGCAGGCCCTGAAAAG (SEQ ID NO:53), the reverse primer is CglobR1: 5'-CGCGGCCCGACCA (SEQ ID NO:54), and the probe is CglobP1: 5'-AGATGTATGCTACTACGCTCGGTGCGACAG (SEQ ID NO:55).

21. The method according to claim 2 wherein the fungi are selected from the group consisting of *Cladosporium cladosporioides* the Type 1, the forward primer is Cclad1F1: 5'-CATTACAAGTGACCCCGGTCTAAC (SEQ ID NO:56), the reverse primer is CcladR1: 5'-CCCCGGAGGCAACAGAG (SEQ ID NO:57), and the probe is CcladP1: 5'-CCGGGATGTTCATAACCCTTTGTTGTCC (SEQ ID NO:58); and for Type 2 the forward primer is Cclad2F1: 5'-TACAAGTGACCCCGGCTACG (SEQ ID NO:59), the reverse primer is CcladR1: 5'CCCCGGAGGCAACAGAG (SEQ ID NO:60), and the probe is CcladP1: 5'-CCGGGATGTTCATAACCCTTTGTTGTCC (SEQ ID NO:61).

22. The method according to claim 2 wherein the fungi are selected from the group consisting of *Cladosporium herbarum*, the forward primer is CherbF1: 5'-AAGAACGCCCGGGCTT (SEQ ID NO:62), the reverse primer is CherbR1: 5'-CGCAAGAGTTTGAAGTGTCCAC (SEQ ID NO:63), and the probe is CherbP1: 5'-CTGGTTATTCATAACCCTTTGTTGTCCGACTCTG (SEQ ID NO:64).

23. The method according to claim 2 wherein the fungi are selected from the group consisting of *Cladosporium sphaerospermum*, the forward primer is CsphaF1: 5'-ACCGGCTGGGTCTTTCG (SEQ ID NO:65), the reverse primer is CsphaR1: 5'-GGGGTTGTTTTACGGCGTG (SEQ ID NO:66), and the probe is CsphaP1: 5'-CCCGCGGCACCCTTTAGCGA (SEQ ID NO:67).

24. The method according to claim 2 wherein the fungi are selected from the group consisting of *Conidiobolus coronatus/incongruus*, the forward primer is NS92F: 5'-CACCGCCCGTCGCTAC (SEQ ID NO:68), the reverse primer is ConiR1: 5'-TGACCAAGTTTGACCAATTTCTCTA (SEQ ID NO:69), and the probe is ConiP1: 5'-ATGGTTTAGTGAGGCCTCTGGATTTGAAGCTT (SEQ ID NO:70).

25. The method according to claim 2 wherein the fungi are selected from the group consisting of *Cunninghamella elegans*, the forward primer is NS92F: 5'-CACCGCCCGTCGCTAC (SEQ ID NO:71), the reverse primer is CunR1: 5'-AATCTAGTTTGCCATAGTTCTCCTCA (SEQ ID NO:72), and the probe is CunP1: 5'-TGAATGGTCATAGTGAGCATGTGGGATCTTT (SEQ ID NO:73).

26. The method according to claim 2 wherein the fungi are selected from the group consisting of *Emericella nidulans/rugulosa/quadrilineata*, the forward primer is AversF1:

5'-CAACCTCCCACCCGTGAC (SEQ ID NO:74), the reverse primer is AniduR1: 5'-CATTGTTGAAAGTTTTGACTGATTTGT (SEQ ID NO:75), and the probe is versP1: 5'-AGACTGCATCACTCTCAGGCATGAAGTTCAG (SEQ ID NO:76).

27. The method according to claim 2 wherein the fungi are selected from the group consisting of *Eurotium mstelodami/chevalieri/herbariorum/rubrum/repens*, the forward primer is EamstF1: 5'-GTGGCGGCACCATGTCT (SEQ ID NO:77), the reverse primer is EamstR1: 5'-CTGGTTAAAAAGATTGGTTGCGA (SEQ ID NO:78), and the probe is EamstP1: 5'-CAGCTGGACCTACGGGAGCGGG (SEQ ID NO:79).

28. The method according to claim 2 wherein the fungi are selected from the group consisting of *Epicoccum nigrum*, the forward primer is EnigrF1: 5'-TTGTAGACTTCGGTCTGCTACCTCTT (SEQ ID NO:80), the reverse primer is EnigrR1: 5'-TGCAACTGCAAAGGGTTTGAAT (SEQ ID NO:81), and the probe is EnigrP1: 5'-CATGTCTTTTGAGTACCTTCGTTTCCTCGGC (SEQ ID NO:82).

29. The method according to claim 2 wherein the fungi are selected from the group consisting of *Geotrichum candidum* strain UAMH 7863, the forward primer is GeoF1: 5'-GATATTTCTTGTGAATTGCAGAAGTGA (SEQ ID NO:83), the reverse primer is GeoR1: 5'-TTGATTCGAAATTTTAGAAGAGCAAA (SEQ ID NO:84), and the probe is GeoP1: 5'-CAATTCCAAGAGAGAAACAACGCTCAAACAAG (SEQ ID NO:85).

30. The method according to claim 2 wherein the fungi are selected from the group consisting of *Geotrichum candidum*, the forward primer is NS92F: 5'-CACCGCCCGTCGCTAC (SEQ ID NO:86), the reverse primer is GcandR1: 5-AGAAAGTTGCCCTCTCCAGTT (SEQ ID NO:87), and the probe is GeoP2: 5'-TCAATCCGGAAGCCTCACTAAGCCATT (SEQ ID NO:88).

31. The method according to claim 2 wherein the fungi are selected from the group consisting of *Geotrichum klebahnii*, the forward primer is NS92F: 5'-CACCGCCCGTCGCTAC (SEQ ID NO:89), the reverse primer is GklebR1: 5'-AAAAGTCGCCCTCTCCTGC (SEQ ID NO:90), and the probe is GeoP2: 5'-TCAATCCGGAAGCCTCACTAAGCCATT (SEQ ID NO:91).

32. The method according to claim 2 wherein the fungi are selected from the group consisting of *Memnoniella echinata*, the forward primer is StacF4 5'-TCCCAAACCCTTATGTGAACC (SEQ ID NO:92), the reverse primer is MemR1: 5'-TGTTTATACCACTCAGACGATACTCAAGT (SEQ ID NO:93), and the probe is MemP1: 5'-CTCGGGCCCGGAGTCAGGC (SEQ ID NO:94).

33. The method according to claim 2 wherein the fungi are selected from the group consisting of *Mortierella polycephala/wolfii*, the forward primer is NS92F: 5'-CACCGCCCGTCGCTAC (SEQ ID NO:95), the reverse primer is MortR1: 5'-TGACCAAGTTTGGATAACTTTTCAG (SEQ ID NO:96), and the probe is MortP1: 5'-CTTAGTGAGGCTTTCGGATTGGATCTAGGCA (SEQ ID NO:97).

34. The method according to claim 2 wherein the fungi are selected from the group consisting of *Mucor mucedo*, the forward primer is NS92F: 5'-CACCGCCCGTCGCTAC (SEQ ID NO:98), the reverse primer is MmuceR1: 5'-CTAAATAATCTAGTTTGCCATAGTTTTCG (SEQ ID NO:99), and the probe is MucP1: 5'-CCGATTGAATGGTTATAGTGAGCATATGGGATC (SEQ ID NO:100).

35. The method according to claim 2 wherein the fungi are selected from the group consisting of *Mucor amphibiorum/circinelloides/heimalis/indicus/mucedo/racemosus/ramosissimus* and *Rhizopus azygosporus/homothalicus/microsporus/oligosporus/oryzae*, the forward primer is NS92F: 5'-CACCGCCCGTCGCTAC (SEQ ID NO:101), the reverse primer is MucR1-1: 5'-CCTAGTTTGCCATAGTTCTCAGCAG (SEQ ID NO:102), and the probe is MucP1: 5'-CCGATTGAATGGTTATAGTGAGCATATGGGATC (SEQ ID NO:103).

36. The method according to claim 2 wherein the fungi are selected from the group consisting of *Myrothecium verrucaria/roridum*, the forward primer is MyroF1: 5'-AGTTTACAAACTCCCAAACCCTTT (SEQ ID NO:104), the reverse primer is MyroR1: 5'-GTGTCACTCAGAGGAGAAAACCA (SEQ ID No:105), and the probe is MyroP1: 5'-CGCCTGGTTCCGGGCCC (SEQ ID NO:106).

37. The method according to claim 2 wherein the fungi are selected from the group consisting of *Paecilomyces lilacinus*, the forward primer is lilaF1: 5'-CCCACTGTGAACCTTACCTCAG (SEQ ID NO:107), the reverse primer is PlilaR1: 5'-GCTTGTGCAACTCAGAGAAGAAAT (SEQ ID NO:108), and the probe is PlilaP1: 5'-CCGCCCGCTGGGCGTAATG (SEQ ID NO:109).

38. The method according to claim 2 wherein the fungi are selected from the group consisting of *Paecilomyces variotii*, the forward primer is PvariF1: 5'-CCCGCCGTGGTTCAC (SEQ IDI NO:110) or the forward primer is PvariF2: 5'-CGAAGACCCCTGGAACG (SEQ ID NO:111), and the reverse primer is PvariR1: 5'-GTTGTTGAAAGTTTTAATTGATTGATTGT (SEQ ID NO:112), and the probe is PvariP1: 5'-CTCAGACGGCAACCTTCCAGGCA (SEQ ID NO:113).

39. The method according to claim 2 wherein the fungi are selected from the group consisting of *Penicillium aurantiogriseum/polonicum/viridicatum/freii/verrucosum\*/hirsutum*, the forward primer is PauraF1: 5'-CGGGCCCGCCTTTAC (SEQ ID NO:114), the reverse primer is PauraR1-1: 5'-GAAAGTTTTAAATAATTTATATTTTCACTCAGAGTT (SEQ ID NO:115), and the probe is PenP2: 5'-CGCGCCCGCCCGAAGACA (SEQ ID NO:116).

40. The method according to claim 2 wherein the fungi are selected from the group consisting of *Penicillium aurantiogriseum/polonicum/viridicatum/freii*, the forward primer is PauraF2: 5'-ACCGAGTGAGGGCCCTT (SEQ ID NO:117), the reverse primer is PauraR6: 5'-CCCGGCGGCCAGTA (SEQ ID NO:118), and the probe is PenP3: 5'-TCCAACCTCCCACCCGTGTTTATTT (SEQ ID NO:119).

41. The method according to claim 2 wherein the fungi are selected from the group consisting of *Penicillium brevicompactum\*/alberechii*, the forward primer is PbrevF1: 5'-CCTTGTTGCTTCGGCGA (SEQ ID NO:120), the reverse primer is PbrevR2: 5'-TCAGACTACAATCTTCAGACAGAGTTCTAA (SEQ ID NO:121), and the probe is PbrevP1: 5'-CCTCCCTTTTGGCTGCCGGG (SEQ ID NO:122).

42. The method according to claim 2 wherein the fungi are selected from the group consisting of *Penicillium chrysogenum/griseofulvum/glandicola/coprophilum/expansum* and *Eupenicillium crustaceum/egyptiacum*, the forward primer is PchryF1: 5'-CGGGCCCGCCTTAAC (SEQ ID NO:123), the reverse primer is PchryR1-1: 5'-GAAAGTTTTAAATAATTTATATTTTCACTCAGAGTA (SEQ ID NO:124) or the reverse primer is PchryR2-1: 5'-GAAAGTTTTAATAATTTATATTTTCACTCAGACCA (SEQ ID NO:125), and the probe is PenP2: 5'-CGCGCCCGCCGAAGACA (SEQ ID NO:126).

43. The method according to claim 2 wherein the fungi are selected from the group consisting of *Penicillium citrinum/sartoryi/westlingi*, the forward primer is PcitrF1: 5'-CCGTGTTGCCCGAACCTA (SEQ ID NO:127), the reverse primer is PcitrR1: 5'-TTGTTGAAAGTTTTAACTAATTTCGTTATAG (SEQ ID NO:128), and the probe is PcitrP2: 5'-CCCTGAACGCTGTCTGAAGTTGCA (SEQ ID NO:129).

44. The method according to claim 2 wherein fungi are selected from the group consisting of *Penicillium corylophilum*, the forward primer is PcoryF1: 5'-GTCCAACCTCCCACCCA (SEQ ID NO:130), the reverse primer is PcoryR3-1: 5'-GCTCAGACTGCAATCTTCAGACTGT (SEQ ID NO:131), and the probe is PcoryP1: 5'-CTGCCCTCTGGCCCGCG (SEQ ID NO:132).

45. The method according to claim 2 wherein the fungi are selected from the group consisting of *Penicillium decumbens*, the forward primer is PdecuF3: 5'-GGCCTCCGTCCTCCTTTG (SEQ ID NO:133), the reverse primer is PdecR3: 5'-AAAGATTGATGTGTTCGGCAG (SEQ ID NO:134), and the Probe is PdecuP2: 5'-CGCCGGCCGGACCTACAGAG (SEQ ID NO:135).

46. The method according to claim 2 wherein the fungi are selected from the group consisting of *Penicillium echinulatum/solitum/camembertii/commune/crustosum*, the forward primer is PchryF1: 5'-CGGGCCCGCCTTAAC (SEQ ID No:136), the reverse primer is PauraR1-1: 5'-GAAATTTTAAATAATTTATATTTTCACTCAGAGTT (SEQ ID NO:137), and the probe is PenP2: 5'-CGCGCCCGCCGAAGACA (SEQ ID NO:138).

47. The method according to claim 2 wherein fungi are selected from the group consisting of *Penicillium expansum/coprophilum*, the forward primer is PauraF2: 5'-ACCGAGTGAGGGCCCTT (SEQ ID NO:139), the reverse primer is PchryR6: 5'-CCCGCCCCCACTT (SEQ ID NO:140), and the probe is PenP3: 5'-TCCAACCTCCCACCCGTGTTTATTT (SEQ ID NO:141).

48. The method according to claim 2 wherein the fungi are selected from the group consisting of *Penicillium fellutanum/charlesii*, the forward primer is PfellF1: 5'-AACCTCCCACCCGTGTATACTTA (SEQ ID NO:142), the reverse primer is PfellR1: 5'-CTTATCGCTCAGACTGCAAGGTA (SEQ ID NO:143), and the probe is PfellP1: CGGTTGCCCCCCGGCG (SEQ ID NO:144).

49. The method according to claim 2 wherein the fungi are selected from the group consisting of *Penicillium janthinellum/raperi*, the forward primer is PjantF2: 5'-CCCACCCGTGTTTATCATACCTA (SEQ ID NO:145), the reverse primer is PjantR2: 5'-TTGAAAGTTTTAACTGATTTAGCTAATCG (SEQ ID NO:146), and the probe is PjantP2: 5'-TGCAATCTTCAGACAGCGTTCAGGG (SEQ ID NO:147).

50. The method according to claim 2 wherein the fungi are selected from the group consisting of *Penicillium madriti/gladioli*, the forward primer is PauraF1: 5'-CGGGCCCGCCTTTAC (SEQ ID NO:148), the reverse primer is PchryR1-1: 5'-GAAAGTTTTAAATAATTTATATTTTCATCAGAGTA (SEQ ID NO:149) or the reverse primer is PchryR2-1: 5'-GAAGTTTTATAATTTATATTTTCACTCAGACCA (SEQ ID NO:150), and the probe is PenP2: 5'-CGCGCCCGCCGAAGACA (SEQ ID NO:151).

51. The method according to claim 2 wherein the fungi are selected from the group consisting of *Penicillium oxalicum*, the forward primer is PoxalF1: 5'-GGGCCCGCCTCACG (SEQ ID NO:152), the reverse primer is PoxalR1: 5'-GTTGTTGAAAGTTTTAACTGATTTAGTCAAGTA (SEQ ID NO:153), and the probe is PoxalP1: 5'-ACAAGAGTTCGTTTGTGTGTCTTCGGCG (SEQ ID NO:154).

52. The method according to claim 2 wherein the fungi are selected from the group consisting of *Penicillium roquefortii*, the forward primer is PchryF1: 5'-CGGGCCCGCCTTAAC (SEQ ID NO:155), the reverse primer is ProquR2: 5'-TTAAATAATTTATATTTGTTCTCAGACTGCAT (SEQ ID NO:156), and the probe is PenP2: 5'-CGCGCCCGCCGAAGACA (SEQ ID NO:157).

53. The method according to claim 2 wherein the fungi are selected from the group consisting of *Penicillium simplicissimum/ochrochloron*, the forward primer is PsimpF1-1; 5'-AACCTCCCACCCTGTTGATT (SEQ ID NO:158), the reverse primer is PsimpR2-1: 5'-GAGATCCGTTGTTGAAAGTTTTATCTG (SEQ ID NO:159) or the reverse primer is PsimpR3-1: 5'-GAGATCCGTTGTTGAAAGTTTTAACAG (SEQ ID NO:160), and the probe is PsimpP1: 5'-CCGCCTCACGGCCGCC (SEQ ID NO:161).

54. The method according to claim 2 wherein the fungi are selected from the group consisting of *Penicillium spinulosum/glabrum/thomii/pupurescens* and *Eupenicillium lapidosum*, the forward primer is PspinF1: 5'-GTACCTTGTTGCTTCGGTGC (SEQ ID NO:162), the reverse primer is PspinR1: 5'-CGTTGTTGAAAGTTTTAACTTATTTAGTTTAT (SEQ ID NO:163), and the probe is PspinP1: 5'-TCCGCGCGCACCGGAG (SEQ ID NO:164).

55. The method according to claim 2 wherein the fungi are selected from the group consisting of *Rhizomucor miehei/pusillus/variabilis*, the forward primer is NS92F: 5'-CACCGCCCGTCGCTAC (SEQ ID NO:165), the reverse primer is RmucR1: 5'-GTAGTTTGCCATAGTTCGGCTA (SEQ ID NO:166), and the probe is RmucP1: 5'-TTGAATGGCTATAGTGAGCATATGGGAGGCT (SEQ ID NO:167).

56. The method according to claim 2 wherein the fungi are selected from the group consisting of *Rhizopus stolonifer*, the forward primer is NS92F: 5'-CACCGCCCGTCGCTAC (SEQ ID NO:168), the reverse primer is RstolR1: 5'-GCTTAGTTTGCCATAGTTCTCTAACAA (SEQ ID NO:169), and the probe is MucP1: 5'-CCGATTGAATGGTTATAGTGAGCATATGGGATC (SEQ ID NO:170).

57. The method according to claim 2 wherein the fungi are selected from the group consisting of *Scopulariopsis asperula*, the forward primer is SCbrvF1: 5'-CCCCTGCGTAGTAGATCCTACAT (SEQ ID NO:171), the reverse primer is SCasprR1: 5'-TCCGAGGTCAAACCATGAGTAA (SEQ ID NO:172)

and the probe is ScopP1: 5'-TCGCATCGGGTCCCGGCG (SEQ ID NO:173).

58. The method according to claim 2 wherein the fungi are selected from the group consisting of *Scopulariopsis brevicaulis/fusca,* the forward primer is SCbrvF1: 5'-CCCCTGCGTAGTAGATCCTACAT (SEQ ID NO:174), the reverse primer is SCbrvR1: 5'-TCCGAGGTCAAACCATGAAATA (SEQ ID NO:175), and the probe is ScopP1: 5'-TCGCATCGGGTCCCGGCG (SEQ ID NO:176).

59. The method according to claim 2 wherein the fungi are selected from the group consisting of *Scopulariopsis brumptii,* the forward primer is SCbrmF1: 5'-CCCCTGCGTAGTAGTARAACCA (SEQ ID NO:177), the reverse primer is SCbrmR1: 5'-CCGAGGTCAAACATCTTTGG (SEQ ID NO:178), and the probe is ScopP1: 5'-TCGCATCGGGTCCCGGCG (SEQ ID NO:179).

60. The method according to claim 2 wherein the fungi are selected from the group consisting of *Scopulariopsis chartarum,* the forward primer is SCchrF1: 5'-CCCCCTGCGTAGTAGTAAAGC (SEQ ID NO:180), the reverse primer is SCchrR1: 5'-TCCGAGGTCAAACCATCAAG (SEQ ID NO:181), and the probe is ScopP1: 5'-TCGCATCGGGTCCCGGCG (SEQ ID NO:182).

61. The method according to claim 2 wherein the fungi are selected from the group consisting of *Scopulariopsis sphaerospora,* the forward primer is SCsphF1: 5'-CCCCCTGCGTAGTAGTTTACAA (SEQ ID NO:183), the reverse primer is SCsphR1: 5'-CCGAGGTCAAACCATCAAAAG (SEQ ID NO:184), and the probe is ScopP1: 5'-TCGCATCGGGTCCCGGCG (SEQ ID NO:185).

62. The method according to claim 2 wherein the fungi are selected from the group consisting of *Stachybotrys chartarum,* the forward primer is StacF4 5'-TCCCAAACCCTTATGTGAACC (SEQ ID NO:186), the reverse primer is StacR5 5'-GTTTGCCACTCAGAGAATACTGAAA (SEQ ID NO:187), and the probe is StacP2 5'-CTGCGCCCGGATCCAGGC (SEQ ID NO:188).

63. The method according to claim 2 wherein the fungi are selected from the group consisting of *Trichoderma asperellum/hamatum,* the forward primer is TasprF1: 5'-CCCAAACCCRATGTGAACGT (SEQ ID NO:189), the reverse primer is TasprR2-1: 5'-GGACTACAGAAAGAGTTTGGTTGCTT (SEQ ID NO:190), and the probe is TridP1: 5'-CCAAACTGTTGCCTCGGCGGG (SEQ ID NO:191).

64. The method according to claim 2 wherein the fungi are selected from the group consisting of *Trichoderma asperellum/hamatum/viride\*,* the forward primer is TasprF1: 5'-CCCAAACCCAATGTGAACGT (SEQ ID NO:192), the reverse primer is TasprR1: 5'-TTTGCTCAGAGCTGTAAGAAATACG (SEQ ID NO:193), and the probe is TridP1: 5'-CCAAACTGTTGCCTCGGCGGG (SEQ ID NO:194).

65. The method according to claim 2 wherein the fungi are selected from the group consisting of *Trichoderma harzianum,* the forward primer is TharzF1: 5'-TTGCCTCGGCGGGAT (SEQ ID NO:195), the reverse primer is TharzR1: 5'-ATTTTCGAAACGCCTACGAGA (SEQ ID NO:196), and the probe TharzP1: 5'-CTGCCCCGGGTGCGTCG (SEQ ID NO:197).

66. The method according to claim 2 wherein the fungi are selected from the group consisting of *Trichoderma longibrachiatum/citroviride,* the forward primer is TlongF1: 5'-TGCCTCGGCGGGATTC (SEQ ID NO:198), the reverse primer is TlongR1: 5'-CGAGAAAGGCTCAGAGCAAAAAT (SEQ ID NO:199), and the probe is TlongP1: 5'-TCGCAGCCCCGGATCCCA (SEQ ID NO:200).

67. The method according to claim 2 wherein the fungi are selected from the group consisting of *Trichoderma viride\*/ atroviride/koningii,* the forward primer is TviriF1: 5'-CCCAAACCCAATGTGAACCA (SEQ ID NO:201), the reverse primer is TviriR1: 5'-TCCGCGAGGGGACTACAG (SEQ ID NO:202), and the probe is TridP1: 5'-CCAAACTGTTGCCTCGGCGGG (SEQ ID NO:203).

68. The method according to claim 2 wherein the fungi are selected from the group consisting of *Ulocladium atrum/ chartarum,* the forward primer is UatrmF1: 5'-GCGGGCTGGCATCCTT (SEQ ID NO:204), the reverse primer is UatrmR1: 5'-TTGTCCTATGGTGGGCGAA (SEQ ID NO:205), and the probe is UloP1: 5'-TGAATTATTCACCCGTGTCTTTTGCGTACTTCT (SEQ ID NO:206).

69. The method according to claim 2 wherein the fungi are selected from the group consisting of *Ulocladium botrytis,* the forward primer is UbotrF1: 5'-CCCCCAGCAGTGCGTT (SEQ ID NO:207), the reverse primer is UbotrR1: 5'-CTGATTGCAATTACAAAAGGTTTATG (SEQ ID NO:208), and the probe is UloP1: 5'-TGAATTATTCACCCGTGTCTTTTGCGTACTTCT (SEQ ID NO:209).

70. The method according to claim 2 wherein the fungi are selected from the group consisting of *Wallemia sebi,* the forward primer is WsebiF1: 5'-GGCTTAGTGAATCCTTCGGAG (SEQ ID NO:210), the reverse primer is WsebiR1: 5'-GTTTACCCAACTTTGCAGTCCA (SEQ ID NO:211), and the probe is WsebiP1: 5'-TGTGCCGTTGCCGGCTCAAATAG (SEQ ID NO:212).

71. The method according to claim 2 wherein the fungi are selected from the group consisting of Universal Fungal Group, for ASSAY 1, the forward primer is 5.8F1: 5'-AACTTTCAACAACGGATCTCTTGG (SEQ ID NO:213), the reverse primer is 5.8R1: 5'-GCGTTCAAAGACTCGATGATTCAC (SEQ ID NO:214), and the probe is 5.8P1: 5'-CATCGATGAAGAACGCAGCGAAATGC (SEQ ID NO:215), for ASSAY 2, the forward primer is NS92F: 5'-CACCGCCCGTCGCTAC (SEQ ID NO:216), the reverse primer is ZygR1: 5'-TAATGATCCTTCCGCAGGTTC (SEQ ID NO:217), and the probe is ZygP1: 5'-CCTACGGAAACCTTGTTACGACTTTTACTTCCTC-TAAA (SEQ ID NO:218).

72. The method according to claim 2 wherein the bacteria are selected from the group consisting of *Escherichia coli,* the forward primer is uidAF1: 5'-GGGCAGGCCAGCGTATC (SEQ ID NO:219), the reverse primer is uidAR1: 5'-CCCACACTTTGCCGTAATGA (SEQ ID NO:220) or the reverse primer is uidAR2; 5'-CGTACACTTTTCCCGGCAAT (SEQ ID NO:221) and the probe is uidAP1: 5'-TGCTGCGTTTCGATGCGGTCA (SEQ ID NO:222).

73. The method according to claim wherein the bacteria are selected from the group consisting of *Helicobacter pylorii*, the forward primer is Hpy1F1: 5'-GGGTATTGAAGCGATGTTTCCT (SEQ ID NO:223), the reverse primer is Hpy1R1: 5'-GCTTTTTTGCCTTCGTTGATAGT (SEQ ID NO:224), and the probe is Hpy1P1: 5'-AAACTCGTAACCGTGCATACCCCTATTGAG (SEQ ID NO:225).

74. The method according to claim 1 wherein the label is a fluorescent label.

75. The method according to claim 1 wherein fungi are detected and quantitated using PCR, hybridization, or other molecular techniques.

76. The method according to claim 2 wherein the primer and probes are used for determining the cell quantities of fungi and bacteria.

77. The method according to claim 1 wherein the analysis is a fluorescent probe.

78. The method according to claim 1 wherein a fungus is detected and the sequence amplified is internal transcribed spacer regions of nuclear ribosomal DNA.

79. The method according to claim 1 wherein a bacterium is detected and the sequence amplified is an enzyme unique to the bacterium.

* * * * *

```
                         SEQUENCE LISTING

<160> NUMBER OF SEQ ID NOS: 225

<210> SEQ ID NO 1
<211> LENGTH: 16
<212> TYPE: DNA
<213> ORGANISM: Absidia coerulea/glauca

<400> SEQUENCE: 1
caccgcccgt cgctac                                                    16

<210> SEQ ID NO 2
<211> LENGTH: 26
<212> TYPE: DNA
<213> ORGANISM: Absidia coerulea/glauca

<400> SEQUENCE: 2
tctagtttgc catagttctc ttccag                                         26

<210> SEQ ID NO 3
<211> LENGTH: 33
<212> TYPE: DNA
<213> ORGANISM: Absidia coerulea/glauca

<400> SEQUENCE: 3
ccgattgaat ggttatagtg agcatatggg atc                                 33

<210> SEQ ID NO 4
<211> LENGTH: 16
<212> TYPE: DNA
<213> ORGANISM: Absidia corymbifera

<400> SEQUENCE: 4
caccgcccgt cgctac                                                    16

<210> SEQ ID NO 5
<211> LENGTH: 20
<212> TYPE: DNA
<213> ORGANISM: Absidia corymbifera

<400> SEQUENCE: 5
gcaaagcgtt ccgaaggaca                                                20

<210> SEQ ID NO 6
<211> LENGTH: 25
<212> TYPE: DNA
<213> ORGANISM: Absidia corymbifera

<400> SEQUENCE: 6
atggcacgag caagcattag ggacg                                          25

<210> SEQ ID NO 7
<211> LENGTH: 24
<212> TYPE: DNA
<213> ORGANISM: Acremonium strictum
```

```
<400> SEQUENCE: 7
caacccattg tgaacttacc aaac                                           24

<210> SEQ ID NO 8
<211> LENGTH: 22
<212> TYPE: DNA
<213> ORGANISM: Acremonium strictum

<400> SEQUENCE: 8
cgcccctcag agaaatacga tt                                             22

<210> SEQ ID NO 9
<211> LENGTH: 18
<212> TYPE: DNA
<213> ORGANISM: Acremonium strictum

<400> SEQUENCE: 9
tcagcgcgcg gtggcctc                                                  18

<210> SEQ ID NO 10
<211> LENGTH: 16
<212> TYPE: DNA
<213> ORGANISM: Alternaria alternata

<400> SEQUENCE: 10
ggcgggctgg aacctc                                                    16

<210> SEQ ID NO 11
<211> LENGTH: 29
<212> TYPE: DNA
<213> ORGANISM: Alternaria alternata

<400> SEQUENCE: 11
gcaattacaa aaggtttatg tttgtcgta                                      29

<210> SEQ ID NO 12
<211> LENGTH: 30
<212> TYPE: DNA
<213> ORGANISM: Alternaria alternata

<400> SEQUENCE: 12
tgcaattact aaaggtttat gtttgtcgta                                     30

<210> SEQ ID NO 13
<211> LENGTH: 34
<212> TYPE: DNA
<213> ORGANISM: Alternaria alternata

<400> SEQUENCE: 13
ttacagcctt gctgaattat tcacccttgt cttt                                34

<210> SEQ ID NO 14
<211> LENGTH: 16
<212> TYPE: DNA
<213> ORGANISM: Apophysomyces elegans and Saksenea vasiformis

<400> SEQUENCE: 14
caccgcccgt cgctac                                                    16

<210> SEQ ID NO 15
<211> LENGTH: 22
<212> TYPE: DNA
```

<213> ORGANISM: Apophysomyces elegans and Saksenea vasiformis

<400> SEQUENCE: 15
gactcgaatg agttctcgct tc                                    22

<210> SEQ ID NO 16
<211> LENGTH: 26
<212> TYPE: DNA
<213> ORGANISM: Apophysomyces elegans and Saksenea vasiformis

<400> SEQUENCE: 16
tggccaagac cagaatatgg gattgc                                26

<210> SEQ ID NO 17
<211> LENGTH: 21
<212> TYPE: DNA
<213> ORGANISM: Aspergillus flavus/oryzae

<400> SEQUENCE: 17
cgagtgtagg gttcctagcg a                                     21

<210> SEQ ID NO 18
<211> LENGTH: 15
<212> TYPE: DNA
<213> ORGANISM: Aspergillus flavus/oryzae

<400> SEQUENCE: 18
ccggcggcca tgaat                                            15

<210> SEQ ID NO 19
<211> LENGTH: 31
<212> TYPE: DNA
<213> ORGANISM: Aspergillus flavus/oryzae

<400> SEQUENCE: 19
tcccacccgt gtttactgta ccttagttgc t                          31

<210> SEQ ID NO 20
<211> LENGTH: 15
<212> TYPE: DNA
<213> ORGANISM: Aspergillus fumigatus, Neosartorya fischeri

<400> SEQUENCE: 20
gcccgccgtt tcgac                                            15

<210> SEQ ID NO 21
<211> LENGTH: 27
<212> TYPE: DNA
<213> ORGANISM: Aspergillus fumigatus, Neosartorya fischeri

<400> SEQUENCE: 21
ccgttgttga aagttttaac tgattac                               27

<210> SEQ ID NO 22
<211> LENGTH: 21
<212> TYPE: DNA
<213> ORGANISM: Aspergillus fumigatus, Neosartorya fischeri

<400> SEQUENCE: 22
cccgccgaag accccaacat g                                     21

<210> SEQ ID NO 23
<211> LENGTH: 17

```
<212> TYPE: DNA
<213> ORGANISM: Aspergillus niger/foetidus/phoenicus

<400> SEQUENCE: 23
gccggagacc ccaacac                                              17

<210> SEQ ID NO 24
<211> LENGTH: 26
<212> TYPE: DNA
<213> ORGANISM: Aspergillus niger/foetidus/phoenicus

<400> SEQUENCE: 24
tgttgaaagt tttaactgat tgcatt                                    26

<210> SEQ ID NO 25
<211> LENGTH: 30
<212> TYPE: DNA
<213> ORGANISM: Aspergillus niger/foetidus/phoenicus

<400> SEQUENCE: 25
aatcaactca gactgcacgc tttcagacag                                30

<210> SEQ ID NO 26
<211> LENGTH: 21
<212> TYPE: DNA
<213> ORGANISM: Aspergillus nomius

<400> SEQUENCE: 26
cgagtgtagg gttcctagcg a                                         21

<210> SEQ ID NO 27
<211> LENGTH: 13
<212> TYPE: DNA
<213> ORGANISM: Aspergillus nomius

<400> SEQUENCE: 27
ccggcggcct tgc                                                  13

<210> SEQ ID NO 28
<211> LENGTH: 31
<212> TYPE: DNA
<213> ORGANISM: Aspergillus nomius

<400> SEQUENCE: 28
tcccacccgt gtttactgta ccttagttgc t                              31

<210> SEQ ID NO 29
<211> LENGTH: 21
<212> TYPE: DNA
<213> ORGANISM: Aspergillus ochraceus/ostianus/auricomus

<400> SEQUENCE: 29
aacctcccac ccgtgtatac c                                         21

<210> SEQ ID NO 30
<211> LENGTH: 15
<212> TYPE: DNA
<213> ORGANISM: Aspergillus ochraceus/ostianus/auricomus

<400> SEQUENCE: 30
ccggcgagcg ctgtg                                                15

<210> SEQ ID NO 31
```

```
<211> LENGTH: 22
<212> TYPE: DNA
<213> ORGANISM: Aspergillus ochraceus/ostianus/auricomus

<400> SEQUENCE: 31
accttgttgc ttcggcgagc cc                                                22

<210> SEQ ID NO 32
<211> LENGTH: 21
<212> TYPE: DNA
<213> ORGANISM: Aspergillus parasiticus/sojae

<400> SEQUENCE: 32
cgagtgtagg gttcctagcg a                                                 21

<210> SEQ ID NO 33
<211> LENGTH: 14
<212> TYPE: DNA
<213> ORGANISM: Aspergillus parasiticus/sojae

<400> SEQUENCE: 33
gcccggggct gacg                                                         14

<210> SEQ ID NO 34
<211> LENGTH: 31
<212> TYPE: DNA
<213> ORGANISM: Aspergillus parasiticus/sojae

<400> SEQUENCE: 34
tcccacccgt gtttactgta ccttagttgc t                                      31

<210> SEQ ID NO 35
<211> LENGTH: 15
<212> TYPE: DNA
<213> ORGANISM: Aspergillus restrictus/caesillus/conicus

<400> SEQUENCE: 35
cgggcccgcc ttcat                                                        15

<210> SEQ ID NO 36
<211> LENGTH: 27
<212> TYPE: DNA
<213> ORGANISM: Aspergillus restrictus/caesillus/conicus

<400> SEQUENCE: 36
gttgttgaaa gttttaacga tttttct                                           27

<210> SEQ ID NO 37
<211> LENGTH: 22
<212> TYPE: DNA
<213> ORGANISM: Aspergillus restrictus/caesillus/conicus

<400> SEQUENCE: 37
cccgccggag actccaacat tg                                                22

<210> SEQ ID NO 38
<211> LENGTH: 18
<212> TYPE: DNA
<213> ORGANISM: Aspergillus sydowii

<400> SEQUENCE: 38
caacctccca cccgtgaa                                                     18
```

-continued

<210> SEQ ID NO 39
<211> LENGTH: 28
<212> TYPE: DNA
<213> ORGANISM: Aspergillus sydowii

<400> SEQUENCE: 39
ccattgttga agttttgac tgatttta                                28

<210> SEQ ID NO 40
<211> LENGTH: 31
<212> TYPE: DNA
<213> ORGANISM: Aspergillus sydowii

<400> SEQUENCE: 40
agactgcatc actctcaggc atgaagttca g                           31

<210> SEQ ID NO 41
<211> LENGTH: 21
<212> TYPE: DNA
<213> ORGANISM: Aspergillus tamarii

<400> SEQUENCE: 41
cgagtgtagg gttcctagcg a                                      21

<210> SEQ ID NO 42
<211> LENGTH: 14
<212> TYPE: DNA
<213> ORGANISM: Aspergillus tamarii

<400> SEQUENCE: 42
cccggcggcc ttaa                                              14

<210> SEQ ID NO 43
<211> LENGTH: 31
<212> TYPE: DNA
<213> ORGANISM: Aspergillus tamarii

<400> SEQUENCE: 43
tcccacccgt gtttactgta ccttagttgc t                           31

<210> SEQ ID NO 44
<211> LENGTH: 20
<212> TYPE: DNA
<213> ORGANISM: Aspergillus terreus

<400> SEQUENCE: 44
ttaccgagtg cgggtcttta                                        20

<210> SEQ ID NO 45
<211> LENGTH: 14
<212> TYPE: DNA
<213> ORGANISM: Aspergillus terreus

<400> SEQUENCE: 45
cggcggccag caac                                              14

<210> SEQ ID NO 46
<211> LENGTH: 29
<212> TYPE: DNA
<213> ORGANISM: Aspergillus terreus

<400> SEQUENCE: 46
aacctcccac ccgtgactat tgtaccttg                              29

<210> SEQ ID NO 47
<211> LENGTH: 22
<212> TYPE: DNA
<213> ORGANISM: Aspergillus ustus

<400> SEQUENCE: 47
gatcattacc gagtgcaggt ct                                              22

<210> SEQ ID NO 48
<211> LENGTH: 18
<212> TYPE: DNA
<213> ORGANISM: Aspergillus ustus

<400> SEQUENCE: 48
gccgaagcaa cgttggtc                                                   18

<210> SEQ ID NO 49
<211> LENGTH: 19
<212> TYPE: DNA
<213> ORGANISM: Aspergillus ustus

<400> SEQUENCE: 49
cccccgggca ggcctaacc                                                  19

<210> SEQ ID NO 50
<211> LENGTH: 14
<212> TYPE: DNA
<213> ORGANISM: Aspergillus versicolor

<400> SEQUENCE: 50
cggcggggag ccct                                                       14

<210> SEQ ID NO 51
<211> LENGTH: 28
<212> TYPE: DNA
<213> ORGANISM: Aspergillus versicolor

<400> SEQUENCE: 51
ccattgttga agttttgac tgatttta                                         28

<210> SEQ ID NO 52
<211> LENGTH: 31
<212> TYPE: DNA
<213> ORGANISM: Aspergillus versicolor

<400> SEQUENCE: 52
agactgcatc actctcaggc atgaagttca g                                    31

<210> SEQ ID NO 53
<211> LENGTH: 17
<212> TYPE: DNA
<213> ORGANISM: Chaetomium globosum

<400> SEQUENCE: 53
ccgcaggccc tgaaaag                                                    17

<210> SEQ ID NO 54
<211> LENGTH: 13
<212> TYPE: DNA
<213> ORGANISM: Chaetomium globosum

<400> SEQUENCE: 54
cgcggcgcga cca                                                        13

<210> SEQ ID NO 55
<211> LENGTH: 30
<212> TYPE: DNA
<213> ORGANISM: Chaetomium globosum

<400> SEQUENCE: 55
agatgtatgc tactacgctc ggtgcgacag                                    30

<210> SEQ ID NO 56
<211> LENGTH: 24
<212> TYPE: DNA
<213> ORGANISM: Cladosporium cladosporioides

<400> SEQUENCE: 56
cattacaagt gaccccggtc taac                                          24

<210> SEQ ID NO 57
<211> LENGTH: 17
<212> TYPE: DNA
<213> ORGANISM: Cladosporium cladosporioides

<400> SEQUENCE: 57
ccccggaggc aacagag                                                  17

<210> SEQ ID NO 58
<211> LENGTH: 28
<212> TYPE: DNA
<213> ORGANISM: Cladosporium cladosporioides

<400> SEQUENCE: 58
ccgggatgtt cataacccttt tgttgtcc                                     28

<210> SEQ ID NO 59
<211> LENGTH: 20
<212> TYPE: DNA
<213> ORGANISM: Cladosporium cladosporioides

<400> SEQUENCE: 59
tacaagtgac cccggctacg                                               20

<210> SEQ ID NO 60
<211> LENGTH: 17
<212> TYPE: DNA
<213> ORGANISM: Cladosporium cladosporioides

<400> SEQUENCE: 60
ccccggaggc aacagag                                                  17

<210> SEQ ID NO 61
<211> LENGTH: 28
<212> TYPE: DNA
<213> ORGANISM: Cladosporium cladosporioides

<400> SEQUENCE: 61
ccgggatgtt cataacccttt tgttgtcc                                     28

<210> SEQ ID NO 62
<211> LENGTH: 16
<212> TYPE: DNA
<213> ORGANISM: Cladosporium herbarum

<400> SEQUENCE: 62
aagaacgccc gggctt                                                          16

<210> SEQ ID NO 63
<211> LENGTH: 22
<212> TYPE: DNA
<213> ORGANISM: Cladosporium herbarum

<400> SEQUENCE: 63
cgcaagagtt tgaagtgtcc ac                                                   22

<210> SEQ ID NO 64
<211> LENGTH: 34
<212> TYPE: DNA
<213> ORGANISM: Cladosporium herbarum

<400> SEQUENCE: 64
ctggttattc ataaccctttt gttgtccgac tctg                                     34

<210> SEQ ID NO 65
<211> LENGTH: 17
<212> TYPE: DNA
<213> ORGANISM: Cladosporium sphaerospermum

<400> SEQUENCE: 65
accggctggg tctttcg                                                         17

<210> SEQ ID NO 66
<211> LENGTH: 19
<212> TYPE: DNA
<213> ORGANISM: Cladosporium sphaerospermum

<400> SEQUENCE: 66
ggggttgttt tacggcgtg                                                       19

<210> SEQ ID NO 67
<211> LENGTH: 20
<212> TYPE: DNA
<213> ORGANISM: Cladosporium sphaerospermum

<400> SEQUENCE: 67
cccgcggcac cctttagcga                                                      20

<210> SEQ ID NO 68
<211> LENGTH: 16
<212> TYPE: DNA
<213> ORGANISM: Conidiobolus coronatus/incongruus

<400> SEQUENCE: 68
caccgcccgt cgctac                                                          16

<210> SEQ ID NO 69
<211> LENGTH: 25
<212> TYPE: DNA
<213> ORGANISM: Conidiobolus coronatus/incongruus

<400> SEQUENCE: 69
tgaccaagtt tgaccaattt ctcta                                                25

<210> SEQ ID NO 70
<211> LENGTH: 32
<212> TYPE: DNA
<213> ORGANISM: Conidiobolus coronatus/incongruus

<400> SEQUENCE: 70

```
atggtttagt gaggcctctg gatttgaagc tt                            32

<210> SEQ ID NO 71
<211> LENGTH: 16
<212> TYPE: DNA
<213> ORGANISM: Cunninghamella elegans

<400> SEQUENCE: 71
caccgcccgt cgctac                                              16

<210> SEQ ID NO 72
<211> LENGTH: 26
<212> TYPE: DNA
<213> ORGANISM: Cunninghamella elegans

<400> SEQUENCE: 72
aatctagttt gccatagttc tcctca                                   26

<210> SEQ ID NO 73
<211> LENGTH: 31
<212> TYPE: DNA
<213> ORGANISM: Cunninghamella elegans

<400> SEQUENCE: 73
tgaatggtca tagtgagcat gtgggatctt t                             31

<210> SEQ ID NO 74
<211> LENGTH: 18
<212> TYPE: DNA
<213> ORGANISM: Emericella nidulans/rugulosa/quadrilinea ta

<400> SEQUENCE: 74
caacctccca cccgtgac                                            18

<210> SEQ ID NO 75
<211> LENGTH: 27
<212> TYPE: DNA
<213> ORGANISM: Emericella nidulans/rugulosa/quadrilinea ta

<400> SEQUENCE: 75
cattgttgaa agttttgact gatttgt                                  27

<210> SEQ ID NO 76
<211> LENGTH: 31
<212> TYPE: DNA
<213> ORGANISM: Emericella nidulans/rugulosa/quadrilinea ta

<400> SEQUENCE: 76
agactgcatc actctcaggc atgaagttca g                             31

<210> SEQ ID NO 77
<211> LENGTH: 17
<212> TYPE: DNA
<213> ORGANISM: Eurotium
         amstelo dami/chevalieri/herbariorum/rubrum/repens

<400> SEQUENCE: 77
gtggcggcac catgtct                                             17

<210> SEQ ID NO 78
<211> LENGTH: 23
<212> TYPE: DNA
<213> ORGANISM: Eurotium
```

-continued amstelo dami/chevalieri/herbariorum/rubrum/repens

<400> SEQUENCE: 78
ctggttaaaa agattggttg cga                                          23

<210> SEQ ID NO 79
<211> LENGTH: 22
<212> TYPE: DNA
<213> ORGANISM: Eurotium
         amstelo dami/chevalieri/herbariorum/rubrum/repens

<400> SEQUENCE: 79
cagctggacc tacgggagcg gg                                           22

<210> SEQ ID NO 80
<211> LENGTH: 26
<212> TYPE: DNA
<213> ORGANISM: Epicoccum nigrum

<400> SEQUENCE: 80
ttgtagactt cggtctgcta cctctt                                       26

<210> SEQ ID NO 81
<211> LENGTH: 22
<212> TYPE: DNA
<213> ORGANISM: Epicoccum nigrum

<400> SEQUENCE: 81
tgcaactgca aagggtttga at                                           22

<210> SEQ ID NO 82
<211> LENGTH: 31
<212> TYPE: DNA
<213> ORGANISM: Epicoccum nigrum

<400> SEQUENCE: 82
catgtctttt gagtaccttc gtttcctcgg c                                 31

<210> SEQ ID NO 83
<211> LENGTH: 27
<212> TYPE: DNA
<213> ORGANISM: Geotrichum candidum strain UAMH 7863

<400> SEQUENCE: 83
gatatttctt gtgaattgca gaagtga                                      27

<210> SEQ ID NO 84
<211> LENGTH: 26
<212> TYPE: DNA
<213> ORGANISM: Geotrichum candidum strain UAMH 7863

<400> SEQUENCE: 84
ttgattcgaa attttagaag agcaaa                                       26

<210> SEQ ID NO 85
<211> LENGTH: 32
<212> TYPE: DNA
<213> ORGANISM: Geotrichum candidum strain UAMH 7863

<400> SEQUENCE: 85
caattccaag agagaaacaa cgctcaaaca ag                                32

<210> SEQ ID NO 86

```
<211> LENGTH: 16
<212> TYPE: DNA
<213> ORGANISM: Geotrichum candidum

<400> SEQUENCE: 86
caccgcccgt cgctac                                                      16

<210> SEQ ID NO 87
<211> LENGTH: 22
<212> TYPE: DNA
<213> ORGANISM: Geotrichum candidum

<400> SEQUENCE: 87
agaaaagttg ccctctccag tt                                               22

<210> SEQ ID NO 88
<211> LENGTH: 27
<212> TYPE: DNA
<213> ORGANISM: Geotrichum candidum

<400> SEQUENCE: 88
tcaatccgga agcctcacta agccatt                                          27

<210> SEQ ID NO 89
<211> LENGTH: 16
<212> TYPE: DNA
<213> ORGANISM: Geotrichum klebahnii

<400> SEQUENCE: 89
caccgcccgt cgctac                                                      16

<210> SEQ ID NO 90
<211> LENGTH: 19
<212> TYPE: DNA
<213> ORGANISM: Geotrichum klebahnii

<400> SEQUENCE: 90
aaaagtcgcc ctctcctgc                                                   19

<210> SEQ ID NO 91
<211> LENGTH: 27
<212> TYPE: DNA
<213> ORGANISM: Geotrichum klebahnii

<400> SEQUENCE: 91
tcaatccgga agcctcacta agccatt                                          27

<210> SEQ ID NO 92
<211> LENGTH: 21
<212> TYPE: DNA
<213> ORGANISM: Memnoniella echinate

<400> SEQUENCE: 92
tcccaaaccc ttatgtgaac c                                                21

<210> SEQ ID NO 93
<211> LENGTH: 29
<212> TYPE: DNA
<213> ORGANISM: Memnoniella echinate

<400> SEQUENCE: 93
tgtttatacc actcagacga tactcaagt                                        29
```

-continued

```
<210> SEQ ID NO 94
<211> LENGTH: 19
<212> TYPE: DNA
<213> ORGANISM: Memnoniella echinate

<400> SEQUENCE: 94
ctcgggcccg gagtcaggc                                                 19

<210> SEQ ID NO 95
<211> LENGTH: 16
<212> TYPE: DNA
<213> ORGANISM: Mortierella polycephala/wolfii

<400> SEQUENCE: 95
caccgcccgt cgctac                                                    16

<210> SEQ ID NO 96
<211> LENGTH: 25
<212> TYPE: DNA
<213> ORGANISM: Mortierella polycephala/wolfii

<400> SEQUENCE: 96
tgaccaagtt tggataactt ttcag                                          25

<210> SEQ ID NO 97
<211> LENGTH: 31
<212> TYPE: DNA
<213> ORGANISM: Mortierella polycephala/wolfii

<400> SEQUENCE: 97
cttagtgagg ctttcggatt ggatctaggc a                                   31

<210> SEQ ID NO 98
<211> LENGTH: 16
<212> TYPE: DNA
<213> ORGANISM: Mucor mucedo

<400> SEQUENCE: 98
caccgcccgt cgctac                                                    16

<210> SEQ ID NO 99
<211> LENGTH: 29
<212> TYPE: DNA
<213> ORGANISM: Mucor mucedo

<400> SEQUENCE: 99
ctaaataatc tagtttgcca tagttttcg                                      29

<210> SEQ ID NO 100
<211> LENGTH: 33
<212> TYPE: DNA
<213> ORGANISM: Mucor mucedo

<400> SEQUENCE: 100
ccgattgaat ggttatagtg agcatatggg atc                                 33

<210> SEQ ID NO 101
<211> LENGTH: 16
<212> TYPE: DNA
<213> ORGANISM: Mucor amphibiorum/circinelloides/heimali s/indicus/
mucedo/racemosus/ramosissimus and Rhizopus azygosporus/homotha licus/
microsporus/oligosporus/oryzae

<400> SEQUENCE: 101
```

```
caccgcccgt cgctac                                               16

<210> SEQ ID NO 102
<211> LENGTH: 25
<212> TYPE: DNA
<213> ORGANISM: Mucor amphibiorum/circinelloides/heimali s/indicus/
mucedo/racemosus/ramosissimus and Rhizopus azygosporus/homotha licus/
microsporus/oligosporus/oryzae

<400> SEQUENCE: 102
cctagtttgc catagttctc agcag                                     25

<210> SEQ ID NO 103
<211> LENGTH: 33
<212> TYPE: DNA
<213> ORGANISM: Mucor amphibiorum/circinelloides/heimali s/indicus/
mucedo/racemosus/ ramosissimus and Rhizopus azygosporus/hom othalicus/
microsporus/oligosporus/oryzae

<400> SEQUENCE: 103
ccgattgaat ggttatagtg agcatatggg atc                            33

<210> SEQ ID NO 104
<211> LENGTH: 24
<212> TYPE: DNA
<213> ORGANISM: Myrothecium verrucaria/roridum

<400> SEQUENCE: 104
agtttacaaa ctcccaaacc cttt                                      24

<210> SEQ ID NO 105
<211> LENGTH: 23
<212> TYPE: DNA
<213> ORGANISM: Myrothecium verrucaria/roridum

<400> SEQUENCE: 105
gtgtcactca gaggagaaaa cca                                       23

<210> SEQ ID NO 106
<211> LENGTH: 17
<212> TYPE: DNA
<213> ORGANISM: Myrothecium verrucaria/roridum

<400> SEQUENCE: 106
cgcctggttc cgggccc                                              17

<210> SEQ ID NO 107
<211> LENGTH: 22
<212> TYPE: DNA
<213> ORGANISM: Paecilomyces lilacinus

<400> SEQUENCE: 107
cccactgtga accttacctc ag                                        22

<210> SEQ ID NO 108
<211> LENGTH: 24
<212> TYPE: DNA
<213> ORGANISM: Paecilomyces lilacinus

<400> SEQUENCE: 108
gcttgtgcaa ctcagagaag aaat                                      24

<210> SEQ ID NO 109
<211> LENGTH: 19
```

```
<212> TYPE: DNA
<213> ORGANISM: Paecilomyces lilacinus

<400> SEQUENCE: 109
ccgcccgctg ggcgtaatg                                              19

<210> SEQ ID NO 110
<211> LENGTH: 15
<212> TYPE: DNA
<213> ORGANISM: Paecilomyces variotii

<400> SEQUENCE: 110
cccgccgtgg ttcac                                                  15

<210> SEQ ID NO 111
<211> LENGTH: 17
<212> TYPE: DNA
<213> ORGANISM: Paecilomyces variotii

<400> SEQUENCE: 111
cgaagacccc tggaacg                                                17

<210> SEQ ID NO 112
<211> LENGTH: 29
<212> TYPE: DNA
<213> ORGANISM: Paecilomyces variotii

<400> SEQUENCE: 112
gttgttgaaa gttttaattg attgattgt                                   29

<210> SEQ ID NO 113
<211> LENGTH: 23
<212> TYPE: DNA
<213> ORGANISM: Paecilomyces variotii

<400> SEQUENCE: 113
ctcagacggc aaccttccag gca                                         23

<210> SEQ ID NO 114
<211> LENGTH: 15
<212> TYPE: DNA
<213> ORGANISM: Penicillium aurantiogriseum/polonicum/vi ridicatum/
      freii/verrucosum/hirsutum

<400> SEQUENCE: 114
cgggcccgcc tttac                                                  15

<210> SEQ ID NO 115
<211> LENGTH: 36
<212> TYPE: DNA
<213> ORGANISM: Penicillium aurantiogriseum/polonicum/vi ridicatum/
      freii/verrucosum/hirsutum

<400> SEQUENCE: 115
gaaagtttta aataatttat attttcactc agagtt                           36

<210> SEQ ID NO 116
<211> LENGTH: 17
<212> TYPE: DNA
<213> ORGANISM: Penicillium aurantiogriseum/polonicum/vi ridicatum/
      freii/verrucosum/hirsutum

<400> SEQUENCE: 116
cgcgcccgcc gaagaca                                                17
```

<210> SEQ ID NO 117
<211> LENGTH: 17
<212> TYPE: DNA
<213> ORGANISM: Penicillium aurantiogriseum/polonicum/vi ridicatum/freii

<400> SEQUENCE: 117
accgagtgag ggccctt					17

<210> SEQ ID NO 118
<211> LENGTH: 14
<212> TYPE: DNA
<213> ORGANISM: Penicillium aurantiogriseum/polonicum/vi ridicatum/freii

<400> SEQUENCE: 118
cccggcggcc agta						14

<210> SEQ ID NO 119
<211> LENGTH: 25
<212> TYPE: DNA
<213> ORGANISM: Penicillium aurantiogriseum/polonicum/vi ridicatum/freii

<400> SEQUENCE: 119
tccaacctcc cacccgtgtt tattt				25

<210> SEQ ID NO 120
<211> LENGTH: 17
<212> TYPE: DNA
<213> ORGANISM: Penicillium brevicompactum/alberechii

<400> SEQUENCE: 120
ccttgttgct tcggcga					17

<210> SEQ ID NO 121
<211> LENGTH: 30
<212> TYPE: DNA
<213> ORGANISM: Penicillium brevicompactum/alberechii

<400> SEQUENCE: 121
tcagactaca atcttcagac agagttctaa			30

<210> SEQ ID NO 122
<211> LENGTH: 20
<212> TYPE: DNA
<213> ORGANISM: Penicillium brevicompactum/alberechii

<400> SEQUENCE: 122
cctgcctttt ggctgccggg					20

<210> SEQ ID NO 123
<211> LENGTH: 15
<212> TYPE: DNA
<213> ORGANISM: Penicillium chrysogenum/griseofulvum/gla ndicola/
coprophilum/expansum and Eupenicillium crustaceum/egyptiacum

<400> SEQUENCE: 123
cgggcccgcc ttaac					15

<210> SEQ ID NO 124
<211> LENGTH: 36
<212> TYPE: DNA
<213> ORGANISM: Penicillium chrysogenum/griseofulvum/gla ndicola/
coprophilum/expansum and Eupenicillium crustaceum/egyptiacum -continued

```
<400> SEQUENCE: 124
gaaagtttta ataatttat attttcactc agagta                          36

<210> SEQ ID NO 125
<211> LENGTH: 36
<212> TYPE: DNA
<213> ORGANISM: Penicillium chrysogenum/griseofulvum/gla ndicola/
      coprophilum/expansum and Eupenicillium crustaceum/egyptiacum

<400> SEQUENCE: 125
gaaagtttta ataatttat attttcactc agacca                          36

<210> SEQ ID NO 126
<211> LENGTH: 17
<212> TYPE: DNA
<213> ORGANISM: Penicillium chrysogenum/griseofulvum/gla ndicola/
      coprophilum/expansum and Eupenicillium crustaceum/egyptiacum

<400> SEQUENCE: 126
cgcgcccgcc gaagaca                                              17

<210> SEQ ID NO 127
<211> LENGTH: 18
<212> TYPE: DNA
<213> ORGANISM: Penicillium citrinum/sartoryi/westlingi

<400> SEQUENCE: 127
ccgtgttgcc cgaaccta                                             18

<210> SEQ ID NO 128
<211> LENGTH: 31
<212> TYPE: DNA
<213> ORGANISM: Penicillium citrinum/sartoryi/westlingi

<400> SEQUENCE: 128
ttgttgaaag ttttaactaa tttcgttata g                              31

<210> SEQ ID NO 129
<211> LENGTH: 25
<212> TYPE: DNA
<213> ORGANISM: Penicillium citrinum/sartoryi/westlingi

<400> SEQUENCE: 129
cccctgaacg ctgtctgaag ttgca                                     25

<210> SEQ ID NO 130
<211> LENGTH: 17
<212> TYPE: DNA
<213> ORGANISM: Penicillium corylophilum

<400> SEQUENCE: 130
gtccaacctc ccaccca                                              17

<210> SEQ ID NO 131
<211> LENGTH: 25
<212> TYPE: DNA
<213> ORGANISM: Penicillium corylophilum

<400> SEQUENCE: 131
gctcagactg caatcttcag actgt                                     25

<210> SEQ ID NO 132
<211> LENGTH: 17
```

```
<212> TYPE: DNA
<213> ORGANISM: Penicillium corylophilum

<400> SEQUENCE: 132
ctgccctctg gcccgcg                                                   17

<210> SEQ ID NO 133
<211> LENGTH: 18
<212> TYPE: DNA
<213> ORGANISM: Penicillium decumbens

<400> SEQUENCE: 133
ggcctccgtc ctcctttg                                                  18

<210> SEQ ID NO 134
<211> LENGTH: 22
<212> TYPE: DNA
<213> ORGANISM: Penicillium decumbens

<400> SEQUENCE: 134
aaaagattga tgtgttcggc ag                                             22

<210> SEQ ID NO 135
<211> LENGTH: 20
<212> TYPE: DNA
<213> ORGANISM: Penicillium decumbens

<400> SEQUENCE: 135
cgccggccgg acctacagag                                                20

<210> SEQ ID NO 136
<211> LENGTH: 15
<212> TYPE: DNA
<213> ORGANISM: Penicillium echinulatum/solitum/camember tii/commune/
crustosum

<400> SEQUENCE: 136
cgggcccgcc ttaac                                                     15

<210> SEQ ID NO 137
<211> LENGTH: 36
<212> TYPE: DNA
<213> ORGANISM: Penicillium echinulatum/solitum/camember tii/commune/
crustosum

<400> SEQUENCE: 137
gaaagtttta aataatttat attttcactc agagtt                              36

<210> SEQ ID NO 138
<211> LENGTH: 17
<212> TYPE: DNA
<213> ORGANISM: Penicillium echinulatum/solitum/camember tii/commune/
crustosum

<400> SEQUENCE: 138
cgcgcccgcc gaagaca                                                   17

<210> SEQ ID NO 139
<211> LENGTH: 17
<212> TYPE: DNA
<213> ORGANISM: Penicillium expansum/coprophilum

<400> SEQUENCE: 139
accgagtgag ggcccttt                                                  17
```

<210> SEQ ID NO 140
<211> LENGTH: 14
<212> TYPE: DNA
<213> ORGANISM: Penicillium expansum/coprophilum

<400> SEQUENCE: 140
cccggcggcc agtt                                                         14

<210> SEQ ID NO 141
<211> LENGTH: 25
<212> TYPE: DNA
<213> ORGANISM: Penicillium expansum/coprophilum

<400> SEQUENCE: 141
tccaacctcc cacccgtgtt tattt                                             25

<210> SEQ ID NO 142
<211> LENGTH: 23
<212> TYPE: DNA
<213> ORGANISM: Penicillium fellutanum/charlesii

<400> SEQUENCE: 142
aacctcccac ccgtgtatac tta                                               23

<210> SEQ ID NO 143
<211> LENGTH: 23
<212> TYPE: DNA
<213> ORGANISM: Penicillium fellutanum/charlesii

<400> SEQUENCE: 143
cttatcgctc agactgcaag gta                                               23

<210> SEQ ID NO 144
<211> LENGTH: 16
<212> TYPE: DNA
<213> ORGANISM: Penicillium fellutanum/charlesii

<400> SEQUENCE: 144
cggttgcccc ccggcg                                                       16

<210> SEQ ID NO 145
<211> LENGTH: 23
<212> TYPE: DNA
<213> ORGANISM: Penicillium janthinellum/raperi

<400> SEQUENCE: 145
cccacccgtg tttatcatac cta                                               23

<210> SEQ ID NO 146
<211> LENGTH: 29
<212> TYPE: DNA
<213> ORGANISM: Penicillium janthinellum/raperi

<400> SEQUENCE: 146
ttgaaagttt taactgattt agctaatcg                                         29

<210> SEQ ID NO 147
<211> LENGTH: 25
<212> TYPE: DNA
<213> ORGANISM: Penicillium janthinellum/raperi

<400> SEQUENCE: 147

-continued

```
tgcaatcttc agacagcgtt caggg                                              25

<210> SEQ ID NO 148
<211> LENGTH: 15
<212> TYPE: DNA
<213> ORGANISM: Penicillium madriti/gladioli

<400> SEQUENCE: 148
cgggcccgcc tttac                                                         15

<210> SEQ ID NO 149
<211> LENGTH: 36
<212> TYPE: DNA
<213> ORGANISM: Penicillium madriti/gladioli

<400> SEQUENCE: 149
gaaagtttta ataatttat attttcactc agagta                                   36

<210> SEQ ID NO 150
<211> LENGTH: 36
<212> TYPE: DNA
<213> ORGANISM: Penicillium madriti/gladioli

<400> SEQUENCE: 150
gaaagtttta ataatttat attttcactc agacca                                   36

<210> SEQ ID NO 151
<211> LENGTH: 17
<212> TYPE: DNA
<213> ORGANISM: Penicillium madriti/gladioli

<400> SEQUENCE: 151
cgcgcccgcc gaagaca                                                       17

<210> SEQ ID NO 152
<211> LENGTH: 14
<212> TYPE: DNA
<213> ORGANISM: Penicillium oxalicum

<400> SEQUENCE: 152
gggcccgcct cacg                                                          14

<210> SEQ ID NO 153
<211> LENGTH: 33
<212> TYPE: DNA
<213> ORGANISM: Penicillium oxalicum

<400> SEQUENCE: 153
gttgttgaaa gttttaactg atttagtcaa gta                                     33

<210> SEQ ID NO 154
<211> LENGTH: 28
<212> TYPE: DNA
<213> ORGANISM: Penicillium oxalicum

<400> SEQUENCE: 154
acaagagttc gtttgtgtgt cttcggcg                                           28

<210> SEQ ID NO 155
<211> LENGTH: 15
<212> TYPE: DNA
<213> ORGANISM: Penicillium roquefortii

<400> SEQUENCE: 155
```

-continued cgggcccgcc ttaac                                              15

<210> SEQ ID NO 156
<211> LENGTH: 32
<212> TYPE: DNA
<213> ORGANISM: Penicillium roquefortii

<400> SEQUENCE: 156
ttaaataatt tatatttgtt ctcagactgc at                           32

<210> SEQ ID NO 157
<211> LENGTH: 17
<212> TYPE: DNA
<213> ORGANISM: Penicillium roquefortii

<400> SEQUENCE: 157
cgcgcccgcc gaagaca                                            17

<210> SEQ ID NO 158
<211> LENGTH: 21
<212> TYPE: DNA
<213> ORGANISM: Penicillium simplicissimum/ochrochloron

<400> SEQUENCE: 158
aacctcccac ccgtgttgat t                                       21

<210> SEQ ID NO 159
<211> LENGTH: 27
<212> TYPE: DNA
<213> ORGANISM: Penicillium simplicissimum/ochrochloron

<400> SEQUENCE: 159
gagatccgtt gttgaaagtt ttatctg                                 27

<210> SEQ ID NO 160
<211> LENGTH: 27
<212> TYPE: DNA
<213> ORGANISM: Penicillium simplicissimum/ochrochloron

<400> SEQUENCE: 160
gagatccgtt gttgaaagtt ttaacag                                 27

<210> SEQ ID NO 161
<211> LENGTH: 16
<212> TYPE: DNA
<213> ORGANISM: Penicillium simplicissimum/ochrochloron

<400> SEQUENCE: 161
ccgcctcacg gccgcc                                             16

<210> SEQ ID NO 162
<211> LENGTH: 20
<212> TYPE: DNA
<213> ORGANISM: Penicillium spinulosum/glabrum/thomii/pu purescens and
Eupenicillium lapidosum

<400> SEQUENCE: 162
gtaccttgtt gcttcggtgc                                         20

<210> SEQ ID NO 163
<211> LENGTH: 32
<212> TYPE: DNA
<213> ORGANISM: Penicillium spinulosum/glabrum/thomii/pu purescens and -continued Eupenicillium lapidosum

<400> SEQUENCE: 163
cgttgttgaa agttttaact tatttagttt at                                       32

<210> SEQ ID NO 164
<211> LENGTH: 16
<212> TYPE: DNA
<213> ORGANISM: Penicillium spinulosum/glabrum/thomii/pu purescens and
Eupenicillium lapidosum

<400> SEQUENCE: 164
tccgcgcgca ccggag                                                         16

<210> SEQ ID NO 165
<211> LENGTH: 16
<212> TYPE: DNA
<213> ORGANISM: Rhizomucor meihei/pusillus/variabilis

<400> SEQUENCE: 165
caccgcccgt cgctac                                                         16

<210> SEQ ID NO 166
<211> LENGTH: 22
<212> TYPE: DNA
<213> ORGANISM: Rhizomucor meihei/pusillus/variabilis

<400> SEQUENCE: 166
gtagtttgcc atagttcggc ta                                                  22

<210> SEQ ID NO 167
<211> LENGTH: 31
<212> TYPE: DNA
<213> ORGANISM: Rhizomucor meihei/pusillus/variabilis

<400> SEQUENCE: 167
ttgaatggct atagtgagca tatgggaggc t                                        31

<210> SEQ ID NO 168
<211> LENGTH: 16
<212> TYPE: DNA
<213> ORGANISM: Rhizopus stolonifer

<400> SEQUENCE: 168
caccgcccgt cgctac                                                         16

<210> SEQ ID NO 169
<211> LENGTH: 27
<212> TYPE: DNA
<213> ORGANISM: Rhizopus stolonifer

<400> SEQUENCE: 169
gcttagtttg ccatagttct ctaacaa                                             27

<210> SEQ ID NO 170
<211> LENGTH: 33
<212> TYPE: DNA
<213> ORGANISM: Rhizopus stolonifer

<400> SEQUENCE: 170
ccgattgaat ggttatagtg agcatatggg atc                                      33

<210> SEQ ID NO 171

```
<211> LENGTH: 23
<212> TYPE: DNA
<213> ORGANISM: Scopulariopsis asperula

<400> SEQUENCE: 171
cccctgcgta gtagatccta cat                                              23

<210> SEQ ID NO 172
<211> LENGTH: 22
<212> TYPE: DNA
<213> ORGANISM: Scopulariopsis asperula

<400> SEQUENCE: 172
tccgaggtca aaccatgagt aa                                               22

<210> SEQ ID NO 173
<211> LENGTH: 18
<212> TYPE: DNA
<213> ORGANISM: Scopulariopsis asperula

<400> SEQUENCE: 173
tcgcatcggg tcccggcg                                                    18

<210> SEQ ID NO 174
<211> LENGTH: 23
<212> TYPE: DNA
<213> ORGANISM: Scopulariopsis brevicaulis/fusca

<400> SEQUENCE: 174
cccctgcgta gtagatccta cat                                              23

<210> SEQ ID NO 175
<211> LENGTH: 22
<212> TYPE: DNA
<213> ORGANISM: Scopulariopsis brevicaulis/fusca

<400> SEQUENCE: 175
tccgaggtca aaccatgaaa ta                                               22

<210> SEQ ID NO 176
<211> LENGTH: 18
<212> TYPE: DNA
<213> ORGANISM: Scopulariopsis brevicaulis/fusca

<400> SEQUENCE: 176
tcgcatcggg tcccggcg                                                    18

<210> SEQ ID NO 177
<211> LENGTH: 22
<212> TYPE: DNA
<213> ORGANISM: Scopulariopsis brumpti

<400> SEQUENCE: 177
cccctgcgta gtagtaaaac ca                                               22

<210> SEQ ID NO 178
<211> LENGTH: 20
<212> TYPE: DNA
<213> ORGANISM: Scopulariopsis brumpti

<400> SEQUENCE: 178
ccgaggtcaa acatctttgg                                                  20
```

-continued

<210> SEQ ID NO 179
<211> LENGTH: 18
<212> TYPE: DNA
<213> ORGANISM: Scopulariopsis brumpti

<400> SEQUENCE: 179
tcgcatcggg tcccggcg                                                18

<210> SEQ ID NO 180
<211> LENGTH: 21
<212> TYPE: DNA
<213> ORGANISM: Scopulariopsis chartarum

<400> SEQUENCE: 180 cccccctgcgt agtagtaaag c                                           21

<210> SEQ ID NO 181
<211> LENGTH: 20
<212> TYPE: DNA
<213> ORGANISM: Scopulariopsis chartarum

<400> SEQUENCE: 181
tccgaggtca aaccatcaag                                              20

<210> SEQ ID NO 182
<211> LENGTH: 18
<212> TYPE: DNA
<213> ORGANISM: Scopulariopsis chartarum

<400> SEQUENCE: 182
tcgcatcggg tcccggcg                                                18

<210> SEQ ID NO 183
<211> LENGTH: 22
<212> TYPE: DNA
<213> ORGANISM: Scopulariopsis sphaerospora

<400> SEQUENCE: 183 cccccctgcgt agtagtttac aa                                          22

<210> SEQ ID NO 184
<211> LENGTH: 21
<212> TYPE: DNA
<213> ORGANISM: Scopulariopsis sphaerospora

<400> SEQUENCE: 184
ccgaggtcaa accatcaaaa g                                            21

<210> SEQ ID NO 185
<211> LENGTH: 18
<212> TYPE: DNA
<213> ORGANISM: Scopulariopsis sphaerospora

<400> SEQUENCE: 185
tcgcatcggg tcccggcg                                                18

<210> SEQ ID NO 186
<211> LENGTH: 21
<212> TYPE: DNA
<213> ORGANISM: Stachybotrys chartarum

<400> SEQUENCE: 186
tcccaaaccc ttatgtgaac c                                            21

```
<210> SEQ ID NO 187
<211> LENGTH: 25
<212> TYPE: DNA
<213> ORGANISM: Stachybotrys chartarum

<400> SEQUENCE: 187
gtttgccact cagagaatac tgaaa                                           25

<210> SEQ ID NO 188
<211> LENGTH: 18
<212> TYPE: DNA
<213> ORGANISM: Stachybotrys chartarum

<400> SEQUENCE: 188
ctgcgcccgg atccaggc                                                   18

<210> SEQ ID NO 189
<211> LENGTH: 20
<212> TYPE: DNA
<213> ORGANISM: Trichoderma asperellum/hamatum

<400> SEQUENCE: 189
cccaaaccca atgtgaacgt                                                 20

<210> SEQ ID NO 190
<211> LENGTH: 26
<212> TYPE: DNA
<213> ORGANISM: Trichoderma asperellum/hamatum

<400> SEQUENCE: 190
ggactacaga aagagtttgg ttgctt                                          26

<210> SEQ ID NO 191
<211> LENGTH: 21
<212> TYPE: DNA
<213> ORGANISM: Trichoderma asperellum/hamatum

<400> SEQUENCE: 191
ccaaactgtt gcctcggcgg g                                               21

<210> SEQ ID NO 192
<211> LENGTH: 20
<212> TYPE: DNA
<213> ORGANISM: Trichoderma asperellum/hamatum/viride

<400> SEQUENCE: 192
cccaaaccca atgtgaacgt                                                 20

<210> SEQ ID NO 193
<211> LENGTH: 25
<212> TYPE: DNA
<213> ORGANISM: Trichoderma asperellum/hamatum/viride

<400> SEQUENCE: 193
tttgctcaga gctgtaagaa atacg                                           25

<210> SEQ ID NO 194
<211> LENGTH: 21
<212> TYPE: DNA
<213> ORGANISM: Trichoderma asperellum/hamatum/viride

<400> SEQUENCE: 194
ccaaactgtt gcctcggcgg g                                               21
```

-continued

```
<210> SEQ ID NO 195
<211> LENGTH: 15
<212> TYPE: DNA
<213> ORGANISM: Trichoderma harzianum

<400> SEQUENCE: 195
ttgcctcggc gggat                                                        15

<210> SEQ ID NO 196
<211> LENGTH: 21
<212> TYPE: DNA
<213> ORGANISM: Trichoderma harzianum

<400> SEQUENCE: 196
attttcgaaa cgcctacgag a                                                 21

<210> SEQ ID NO 197
<211> LENGTH: 17
<212> TYPE: DNA
<213> ORGANISM: Trichoderma harzianum

<400> SEQUENCE: 197
ctgccccggg tgcgtcg                                                      17

<210> SEQ ID NO 198
<211> LENGTH: 16
<212> TYPE: DNA
<213> ORGANISM: Trichoderma longibrachiatum/citreoviride

<400> SEQUENCE: 198
tgcctcggcg ggattc                                                       16

<210> SEQ ID NO 199
<211> LENGTH: 23
<212> TYPE: DNA
<213> ORGANISM: Trichoderma longibrachiatum/citreoviride

<400> SEQUENCE: 199
cgagaaaggc tcagagcaaa aat                                               23

<210> SEQ ID NO 200
<211> LENGTH: 18
<212> TYPE: DNA
<213> ORGANISM: Trichoderma longibrachiatum/citreoviride

<400> SEQUENCE: 200
tcgcagcccc ggatccca                                                     18

<210> SEQ ID NO 201
<211> LENGTH: 20
<212> TYPE: DNA
<213> ORGANISM: Trichoderma viride/atroviride/koningii

<400> SEQUENCE: 201
cccaaaccca atgtgaacca                                                   20

<210> SEQ ID NO 202
<211> LENGTH: 18
<212> TYPE: DNA
<213> ORGANISM: Trichoderma viride/atroviride/koningii

<400> SEQUENCE: 202
```
tccgcgaggg gactacag                     18

<210> SEQ ID NO 203
<211> LENGTH: 21
<212> TYPE: DNA
<213> ORGANISM: Trichoderma viride/atroviride/koningii

<400> SEQUENCE: 203
ccaaactgtt gcctcggcgg g                 21

<210> SEQ ID NO 204
<211> LENGTH: 16
<212> TYPE: DNA
<213> ORGANISM: Ulocladium atrum/chartarum

<400> SEQUENCE: 204
gcgggctggc atcctt                       16

<210> SEQ ID NO 205
<211> LENGTH: 19
<212> TYPE: DNA
<213> ORGANISM: Ulocladium atrum/chartarum

<400> SEQUENCE: 205
ttgtcctatg gtgggcgaa                    19

<210> SEQ ID NO 206
<211> LENGTH: 33
<212> TYPE: DNA
<213> ORGANISM: Ulocladium atrum/chartarum

<400> SEQUENCE: 206
tgaattattc acccgtgtct tttgcgtact tct     33

<210> SEQ ID NO 207
<211> LENGTH: 16
<212> TYPE: DNA
<213> ORGANISM: Ulocladium botrytis

<400> SEQUENCE: 207
cccccagcag tgcgtt                       16

<210> SEQ ID NO 208
<211> LENGTH: 26
<212> TYPE: DNA
<213> ORGANISM: Ulocladium botrytis

<400> SEQUENCE: 208
ctgattgcaa ttacaaaagg tttatg             26

<210> SEQ ID NO 209
<211> LENGTH: 33
<212> TYPE: DNA
<213> ORGANISM: Ulocladium botrytis

<400> SEQUENCE: 209
tgaattattc acccgtgtct tttgcgtact tct     33

<210> SEQ ID NO 210
<211> LENGTH: 21
<212> TYPE: DNA
<213> ORGANISM: Wallemia sebi

<400> SEQUENCE: 210

```
ggcttagtga atccttcgga g                                          21

<210> SEQ ID NO 211
<211> LENGTH: 22
<212> TYPE: DNA
<213> ORGANISM: Wallemia sebi

<400> SEQUENCE: 211
gtttacccaa ctttgcagtc ca                                         22

<210> SEQ ID NO 212
<211> LENGTH: 23
<212> TYPE: DNA
<213> ORGANISM: Wallemia sebi

<400> SEQUENCE: 212
tgtgccgttg ccggctcaaa tag                                        23

<210> SEQ ID NO 213
<211> LENGTH: 24
<212> TYPE: DNA
<213> ORGANISM: Universal Fungal

<400> SEQUENCE: 213
aactttcaac aacggatctc ttgg                                       24

<210> SEQ ID NO 214
<211> LENGTH: 24
<212> TYPE: DNA
<213> ORGANISM: Universal Fungal

<400> SEQUENCE: 214
gcgttcaaag actcgatgat tcac                                       24

<210> SEQ ID NO 215
<211> LENGTH: 26
<212> TYPE: DNA
<213> ORGANISM: Universal Fungal

<400> SEQUENCE: 215
catcgatgaa gaacgcagcg aaatgc                                     26

<210> SEQ ID NO 216
<211> LENGTH: 16
<212> TYPE: DNA
<213> ORGANISM: Universal Fungal

<400> SEQUENCE: 216
caccgcccgt cgctac                                                16

<210> SEQ ID NO 217
<211> LENGTH: 21
<212> TYPE: DNA
<213> ORGANISM: Universal Fungal

<400> SEQUENCE: 217
taatgatcct tccgcaggtt c                                          21

<210> SEQ ID NO 218
<211> LENGTH: 38
<212> TYPE: DNA
<213> ORGANISM: Universal Fungal
```

<400> SEQUENCE: 218
cctacggaaa ccttgttacg acttttactt cctctaaa          38

<210> SEQ ID NO 219
<211> LENGTH: 17
<212> TYPE: DNA
<213> ORGANISM: Escherichia coli

<400> SEQUENCE: 219
gggcaggcca gcgtatc          17

<210> SEQ ID NO 220
<211> LENGTH: 20
<212> TYPE: DNA
<213> ORGANISM: Escherichia coli

<400> SEQUENCE: 220
cccacacttt gccgtaatga          20

<210> SEQ ID NO 221
<211> LENGTH: 20
<212> TYPE: DNA
<213> ORGANISM: Escherichia coli

<400> SEQUENCE: 221
cgtacacttt tcccggcaat          20

<210> SEQ ID NO 222
<211> LENGTH: 21
<212> TYPE: DNA
<213> ORGANISM: Escherichia coli

<400> SEQUENCE: 222
tgctgcgttt cgatgcggtc a          21

<210> SEQ ID NO 223
<211> LENGTH: 22
<212> TYPE: DNA
<213> ORGANISM: Helicobacter pylorii

<400> SEQUENCE: 223
gggtattgaa gcgatgtttc ct          22

<210> SEQ ID NO 224
<211> LENGTH: 23
<212> TYPE: DNA
<213> ORGANISM: Helicobacter pylorii

<400> SEQUENCE: 224
gcttttttgc cttcgttgat agt          23

<210> SEQ ID NO 225
<211> LENGTH: 30
<212> TYPE: DNA
<213> ORGANISM: Helicobacter pylorii

<400> SEQUENCE: 225
aaactcgtaa ccgtgcatac ccctattgag          30